United States Patent
Grimm et al.

(10) Patent No.: US 11,384,398 B2
(45) Date of Patent: Jul. 12, 2022

(54) ASSAY FOR DETECTING HUMAN PAPILLOMA VIRUS (HPV)

(71) Applicant: Abbott Molecular Inc., Des Plaines, IL (US)

(72) Inventors: Wesley Grimm, Des Plaines, IL (US);
Joshua Kostera, Des Plaines, IL (US);
Robert Hillman, Des Plaines, IL (US);
Hong Wang, Des Plaines, IL (US);
Ning Tang, Des Plaines, IL (US);
Shihai Huang, Des Plaines, IL (US);
Klara Abravaya, Des Plaines, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 222 days.

(21) Appl. No.: 16/719,538

(22) Filed: Dec. 18, 2019

(65) Prior Publication Data
US 2020/0199678 A1    Jun. 25, 2020

Related U.S. Application Data

(60) Provisional application No. 62/781,230, filed on Dec. 18, 2018.

(51) Int. Cl.
| | | |
|---|---|---|
| *C12Q 1/68* | (2018.01) | |
| *C12Q 1/6883* | (2018.01) | |
| *C12Q 1/6853* | (2018.01) | |
| *G01N 21/64* | (2006.01) | |

(52) U.S. Cl.
CPC .......... *C12Q 1/6883* (2013.01); *C12Q 1/6853* (2013.01); *G01N 21/6428* (2013.01); *C12Q 2563/107* (2013.01); *G01N 2021/6432* (2013.01); *G01N 2333/025* (2013.01)

(58) Field of Classification Search
CPC ....................................................... C12Q 1/68
USPC ....................................................... 435/6.12
See application file for complete search history.

(56) References Cited

U.S. PATENT DOCUMENTS

| | | | |
|---|---|---|---|
| 4,849,332 A | 7/1989 | Lorinez | |
| 5,364,758 A | 11/1994 | Meijer et al. | |
| 5,705,627 A | 1/1998 | Manos et al. | |
| 5,981,173 A | 11/1999 | Orth et al. | |
| 6,265,154 B1 | 7/2001 | Kroeger et al. | |
| 9,090,948 B2 | 7/2015 | Abravaya et al. | |
| 2010/0081124 A1* | 4/2010 | Abravaya | C12Q 1/708 435/5 |
| 2010/0304360 A1 | 12/2010 | Riccelli et al. | |

FOREIGN PATENT DOCUMENTS

| | | |
|---|---|---|
| WO | WO 2010/039809 A2 | 4/2010 |
| WO | WO 2016/026453 A2 | 2/2016 |
| WO | WO 2016/162555 A1 | 10/2016 |

OTHER PUBLICATIONS

Graham, Human papillomavirus: gene expression, regulation and prospects for novel diagnostic methods and antiviral therapies. Future Microbiol. Oct. 2010;5(10): 1493-506.

Kleter et al., Novel short-fragment PCR assay for highly sensitive broad-spectrum detection of anogenital human papillomaviruses. Am J Pathol. Dec. 1998;153(6): 1731-9.

International Search Report and Written Opinion for PCT/US2019/067215. dated Mar. 17, 2020. 13 pages.

* cited by examiner

*Primary Examiner* — Aaron A Priest
(74) *Attorney, Agent, or Firm* — Casimir Jones S.C.; Lisa Mueller

(57) ABSTRACT

The disclosure is directed to kits and methods for amplifying and detecting human papilloma virus (HPV) of genotype 16, 18, 31, 33, 35, 39, 45, 51, 52, 56, 58, 59, 66, and/or 68 in a sample, which comprises a variety of combinations of forward oligonucleotide primers, reverse oligonucleotide primers, and oligonucleotide probes.

9 Claims, No Drawings

Specification includes a Sequence Listing.

ASSAY FOR DETECTING HUMAN PAPILLOMA VIRUS (HPV)

CROSS-REFERENCE TO RELATED APPLICATIONS

This patent application claims the benefit of U.S. Provisional Patent Application No. 62/781,230, filed Dec. 18, 2018, which is incorporated by reference herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 10,773 Byte ASCII (Text) file named "37420-202_ST25.TXT," created on Dec. 18, 2019.

BACKGROUND OF THE INVENTION

Papillomaviruses are DNA viruses that infect the skin and mucous membranes of humans and animals. Approximately 130 types of human papillomaviruses (HPV) have been identified, of which between 30-40 types are transmitted through sexual contact and infect the anogenital region. Some of these HPV types cause genital warts, while others do not cause any noticeable signs of infection. At least 14 HPV genotypes have been associated with a high risk for cervical cancer, namely genotypes 16, 18, 31, 33, 35, 39, 45, 51, 52, 56, 58, 59, 66 and 68. As such, detection of these high-risk types of HPV is important in the prevention of cervical cancer.

The genomes of all HPV genotypes share a similar organization and encode several early (E) and late (L) proteins. E1 and E2 proteins are required for DNA replication. E4 and E5 proteins are required for replication of the viral genome in the upper layers of the epithelium. E6 and E7 proteins are oncogenic and cooperate to immortalize cells and to induce genomic instability. L1 and L2 proteins form the viral capsid and are expressed late in infection in the upper layers of the epithelium. The long-control-region (LCR) of the genome contains most of the regulatory DNA sequences needed for proper replication of the viral genome and expression of the viral genes.

A variety of methods for detecting high risk types of HPV have been developed, many of which rely upon the detection of unique sequences in the HPV genome (see, e.g., U.S. Pat. Nos. 4,849,332; 5,364,758; 5,705,627; 6,265,154; and 9,090,948; and Kleter, B. et al., *Am. J. of Pathology*, 153(6): 1731-39 (1998)). However, there remains a need for HPV detection methods and systems that: (i) are capable of detecting multiple HPV genotypes in a single reaction while at the same time differentiating the detection of certain specific genotypes from others (e.g., partial genotyping), (ii) are provided in a format that eliminates or reduces storage requirements and PCR reagent waste, and (iii) may be performed quickly. The present disclosure provides such methods and systems.

BRIEF SUMMARY OF THE INVENTION

The disclosure provides a set of oligonucleotide sequences for amplifying and detecting human papilloma virus (HPV) of genotype 16, 18, 31, 33, 35, 39, 45, 51, 52, 56, 58, 59, 66, and/or 68 in a sample. The set comprises: (a) forward primer oligonucleotide sequences comprising SEQ ID NO: 1, SEQ ID NO: 2, SEQ ID NO: 3, and SEQ ID NO: 4; (b) reverse primer oligonucleotide sequences comprising SEQ ID NO: 5 and SEQ ID NO: 6; (c) a first probe oligonucleotide sequence comprising SEQ ID NO: 7 or SEQ ID NO: 25 which specifically hybridizes to HPV genotype 16; (d) a second probe oligonucleotide sequence comprising SEQ ID NO: 8 which specifically hybridizes to HPV genotype 18; (e) a third probe oligonucleotide sequence comprising SEQ ID NO: 9 or SEQ ID NO: 26 which specifically hybridizes to HPV genotype 31; (f) a fourth probe oligonucleotide sequence comprising SEQ ID NO: 10 or SEQ ID NO: 27 which specifically hybridizes to HPV genotype 33; (g) a fifth probe oligonucleotide sequence comprising SEQ ID NO: 11 which specifically hybridizes to HPV genotype 45; (h) a sixth probe oligonucleotide sequence comprising SEQ ID NO: 12 or SEQ ID NO: 28 which specifically hybridizes to HPV genotype 52; (i) a seventh probe oligonucleotide sequence comprising SEQ ID NO: 13 or SEQ ID NO: 29 which specifically hybridizes to HPV genotype 58; (j) an eighth probe oligonucleotide sequence comprising SEQ ID NO: 14 which specifically hybridizes to HPV genotype 35; (k) a ninth probe oligonucleotide sequence comprising SEQ ID NO: 15 or SEQ ID NO: 30 which specifically hybridizes to HPV genotype 39; (l) a tenth probe oligonucleotide sequence comprising SEQ ID NO: 16 or SEQ ID NO: 31 which specifically hybridizes to HPV genotype 51; (m) an eleventh probe oligonucleotide sequence comprising SEQ ID NO: 17 or SEQ ID NO: 32 which specifically hybridizes to HPV genotype 56; (n) a twelfth probe oligonucleotide sequence comprising SEQ ID NO: 18 which specifically hybridizes to HPV genotype 59; (o) a thirteenth probe oligonucleotide sequence comprising SEQ ID NO: 19 which specifically hybridizes to HPV genotype 66; (p) a fourteenth probe oligonucleotide sequence comprising SEQ ID NO: 20 which specifically hybridizes to HPV genotype 68a; and (q) a fifteenth probe oligonucleotide sequence comprising SEQ ID NO: 21 which specifically hybridizes to HPV genotype 68b, wherein each of the probe oligonucleotide sequences of (c)-(q) comprises a detectable label.

The disclosure also provides kits comprising the above-described primer and probe set, as well as methods for detecting HPV of genotype 16, 18, 31, 33, 35, 39, 45, 51, 52, 56, 58, 59, 66, and/or 68 in a sample.

DETAILED DESCRIPTION OF THE INVENTION

The present disclosure is predicated, at least in part, on the development of a collection of primer and probe oligonucleotide sequences that can rapidly detect fourteen high-risk HPV genotypes in a single reaction. The rapid turnaround time is achieved using fast sample preparation chemistry and fast PCR chemistry. In addition, unlike other nucleic acid tests, the assay described herein is compatible with lyophilization, eliminating the need for frozen storage. Compatibility with lyophilization also allows for delivery of the assay in unit-dose format, such that users may run the exact number of tests needed for an application with reduced PCR reagent waste.

The disclosure provides a set of oligonucleotides for amplifying and detecting human papilloma virus (HPV) in a sample. The term "oligonucleotide," as used herein, refers to a short nucleic acid sequence comprising from about 2 to about 100 nucleotides (e.g., about 5, 10, 15, 20, 25, 30, 35, 40, 45, 50, 55, 60, 65, 70, 75, 80, 85, 90, 95, 99, or 100 nucleotides, or a range defined by any of the foregoing values). The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, for example, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

Oligonucleotides can be single-stranded or double-stranded or can contain portions of both double-stranded and single-stranded sequences. The oligonucleotide can be DNA, both genomic and complimentary DNA (cDNA), RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Oligonucleotides can be obtained by chemical synthesis methods or by recombinant methods.

Primer and Probe Oligonucleotides

Oligonucleotides are used in a variety of applications in biotechnology, such as, for example, artificial gene synthesis, as polymerase chain reaction (PCR) primers, in DNA sequencing, and as molecular probes. In one embodiment, the oligonucleotides described herein may be used as primers for nucleic acid amplification or as probes for nucleic acid hybridization and detection. The terms "primer," "primer sequence," and "primer oligonucleotide," as used herein, refer to an oligonucleotide which is capable of acting as a point of initiation of synthesis of a primer extension product that is a complementary strand of nucleic acid (all types of DNA or RNA) when placed under suitable amplification conditions (e.g., buffer, salt, temperature and pH) in the presence of nucleotides and an agent for nucleic acid polymerization (e.g., a DNA-dependent or RNA-dependent polymerase). A primer can be single-stranded or double-stranded. If double-stranded, the primer may first be treated (e.g., denatured) to allow separation of its strands before being used to prepare extension products. Such a denaturation step is typically performed using heat, but may alternatively be carried out using alkali, followed by neutralization. The primers of the present disclosure can be of any suitable size, and desirably comprise, consist essentially of, or consist of about 15 to 50 nucleotides, preferably about 20 to 40 nucleotides, and more preferably about 22 to 30 nucleotides. The primers of the present disclosure can contain additional nucleotides in addition to those described herein. For example, depending on the type of amplification process employed, primers can include, for example, a restriction endonuclease recognition site 5' to the target binding sequence (see, e.g., U.S. Pat. Nos. 5,270,184 and 5,455,166), or an RNA polymerase promoter linked to the target binding sequence of the primer. A "forward primer" is a primer that hybridizes (or anneals) to a target nucleic acid sequence (e.g., template strand) for amplification. A "reverse primer" is a primer that hybridizes (or anneals) to the complementary strand of the target sequence during amplification. A forward primer hybridizes with a target sequence 5' with respect to a reverse primer.

The terms "probe," "probe sequence," and "probe oligonucleotide," refer to an oligonucleotide that can selectively hybridize to at least a portion of a target sequence (e.g., a portion of a target sequence that has been amplified) under appropriate hybridization conditions. In general, a probe sequence is identified as being either "complementary" (i.e., complementary to the coding or sense strand (+)), or "reverse complementary" (i.e., complementary to the anti-sense strand (−)). The probes of the present disclosure can be of any suitable size, and desirably comprise, consist essentially of, or consist of about 10-50 nucleotides, preferably about 12-35 nucleotides, and more preferably about 14-25 nucleotides.

As used herein, the terms "set," "primer set," "probe set," and "primer and probe set," refer to two or more oligonucleotide primers which together are capable of priming the amplification of a target sequence or target nucleic acid of interest (e.g., a target sequence within HPV) and/or at least one probe which can detect the target sequence or target nucleic acid. In certain embodiments, the term "primer set" refers to a pair of primers including a forward primer (or 5' (upstream) primer) that hybridizes with the 5'-end of the target sequence or target nucleic acid to be amplified and a reverse primer (or 3' (downstream) primer) that hybridizes with the complement of the target sequence or target nucleic acid to be amplified. In other embodiments, a primer and probe set may include multiple primers and probes, which can amplify and detect multiple target nucleic acid sequences from an organism of a single strain or type (e.g., two or more early and/or late genes from HPV16), or a single target nucleic acid present in multiple organisms of different strains or types (e.g., the L1 region of HPV16, HPV18, and HPV45).

The set of oligonucleotides described herein may be used to amplify and detect one or more (e.g., 1, 2, 3, 4, 5, 6, 7, 8, 9, 10, 11, 12, 13, 14, 15, or more) target HPV nucleic acid sequences in a sample. The terms "target sequence" and "target nucleic acid" are used interchangeably herein and refer to a specific nucleic acid sequence, the presence or absence of which is to be detected by the disclosed method. In the context of the present disclosure, a target sequence preferably includes a nucleic acid sequence to which one or more primers will hybridize and from which amplification will initiate. The target sequence can also include a probe-hybridizing region with which a probe may form a stable hybrid under appropriate amplification conditions. A target sequence may be single-stranded or double-stranded. The primer and probe sequences described herein can target any suitable nucleic acid sequence or combination of sequences present in the genome of a single HPV genotype, or multiple HPV genotypes or strains, present in a sample.

All HPV are non-enveloped double stranded DNA viruses. Their genomes are circular and approximately 8 kilobase pairs in size. Most encode eight major proteins, six of which are located in the "early" region, and two of which are located in the "late" region (see, e.g., Graham, S. V., *Future Microbiol.*, 5(10): 1493-1506 (2010)). The "early" proteins have regulatory functions and are involved in, for example, HPV genome replication and transcription, control of cell cycle, cell signaling, and apoptosis, immune modulation, and structural modification of the infected cell. Most of the early proteins are expressed throughout the infectious cycle. E4 is the first virus protein expressed late in infection (Doorbar et al., *Virol.*, 238: 40-52 (1997)) followed by the late proteins, L1 and L2, which are specifically expressed in the granular layer of the epithelium. The L1 and L2 proteins comprise the virus capsid, which is required for virus transmission, spread, and survival in the environment. HPV 16 and HPV 18 cause about 70% of cervical cancers and are transmitted directly through sexual contact. The set of oligonucleotides described herein may comprise, consist essentially of, or consist of any number of primer and probe oligonucleotides so as to amplify and detect any suitable number of HPV nucleic acid sequences from any one or combination of HPV genotypes, such as HPV genotypes 16, 18, 31, 33, 35, 39, 45, 51, 52, 56, 58, 59, 66 and/or 68, or combinations thereof. In one embodiment, the set of oligonucleotides described herein comprises, consists essentially of, or consists of primers which amplify at least a portion of the L1 gene region of the genome of any one, or combination of, HPV genotypes 16, 18, 31, 33, 35, 39, 45, 51, 52, 56, 58, 59, 66 and 68, to produce a single HPV amplicon corresponding to each HPV genotype present in the sample, and a probe which hybridizes to the HPV amplicon. In this regard, the primer and probe oligonucleotide sequences ideally are specific to individual HPV genotypes present in a sample (i.e., HPV types 16, 18, 31, 33, 35, 39, 45, 51, 52, 56, 58, 59, 66 and/or 68). As used herein, the term "amplicon" refers to a product of a natural or artificial amplification reaction. A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides.

In one embodiment, the set of oligonucleotides described herein comprises, consists essentially of, or consists of (a) forward primer oligonucleotide sequences comprising SEQ ID NO: 1, SEQ ID NO: 2, SEQ ID NO: 3, and SEQ ID NO: 4; (b) reverse primer oligonucleotide sequences comprising SEQ ID NO: 5 and SEQ ID NO: 6; (c) a first probe oligonucleotide sequence comprising SEQ ID NO: 7 or SEQ ID NO: 25 which specifically hybridizes to HPV genotype 16; (d) a second probe oligonucleotide sequence comprising SEQ ID NO: 8 which specifically hybridizes to HPV genotype 18; (e) a third probe oligonucleotide sequence comprising SEQ ID NO: 9 or SEQ ID NO: 26 which specifically hybridizes to HPV genotype 31; (f) a fourth probe oligonucleotide sequence comprising SEQ ID NO: 10 or SEQ ID NO: 27 which specifically hybridizes to HPV genotype 33; (g) a fifth probe oligonucleotide sequence comprising SEQ ID NO: 11 which specifically hybridizes to HPV genotype 45; (h) a sixth probe oligonucleotide sequence comprising SEQ ID NO: 12 or SEQ ID NO: 28 which specifically hybridizes to HPV genotype 52; (i) a seventh probe oligonucleotide sequence comprising SEQ ID NO: 13 or SEQ ID NO: 29 which specifically hybridizes to HPV genotype 58; (j) an eighth probe oligonucleotide sequence comprising SEQ ID NO: 14 which specifically hybridizes to HPV genotype 35; (k) a ninth probe oligonucleotide sequence comprising SEQ ID NO: 15 or SEQ ID NO: 30 which specifically hybridizes to HPV genotype 39; (l) a tenth probe oligonucleotide sequence comprising SEQ ID NO: 16 or SEQ ID NO: 31 which specifically hybridizes to HPV genotype 51; (m) an eleventh probe oligonucleotide sequence comprising SEQ ID NO: 17 or SEQ ID NO: 32 which specifically hybridizes to HPV genotype 56; (n) a twelfth probe oligonucleotide sequence comprising SEQ ID NO: 18 which specifically hybridizes to HPV genotype 59; (o) a thirteenth probe oligonucleotide sequence comprising SEQ ID NO: 19 which specifically hybridizes to HPV genotype 66; (p) a fourteenth probe oligonucleotide sequence comprising SEQ ID NO: 20 which specifically hybridizes to HPV genotype 68a; and (q) a fifteenth probe oligonucleotide sequence comprising SEQ ID NO: 21 which specifically hybridizes to HPV genotype 68b. The aforementioned set of oligonucleotides also referred to as ALINITY m™ High Risk (HR) HPV Assay.

Any one or combination of the oligonucleotides described herein may be modified in any suitable manner so as to stabilize or enhance the binding affinity (also referred to as "melting temperature" or "$T_m$") of a primer or probe oligonucleotide for its target. In this respect, an oligonucleotide sequence as described herein may comprise one or more modified oligonucleotide bases. For example, the oligonucleotide sequence may comprise one or more propyne-modified bases, wherein the oligonucleotide comprises an alkyne with the chemical formula $CH_3C{\equiv}CH$. The one or more propyne-modified bases may include, for example, 5-(1-propynyl)-2'-deoxy-Uridine (pdU) and/or 5-(1-propynyl)-2'-deoxyCytidine (pdC). In some embodiments, for example, certain probe oligonucleotide sequences described above may comprise a propyne modified sequence as set forth in Table 1.

TABLE 1

| HPV Genotype Specificity | Sequence (5' to 3') Propyne-modified nucleotides indicated in bold | Non-Propyne Modified SEQ ID NO | Propyne Modified SEQ ID NO |
|---|---|---|---|
| Propyne-Modified Probe Oligonucleotide Sequences | | | |
| HPV16 | CTGCCATATCTACTTCAGAA | 7 | 25 |
| HPV31 | AAGTAGTAATTTTAAAGAGT | 9 | 26 |
| HPV33 | ATGCACACAAGTAACTAGT | 10 | 27 |
| HPV52 | AAAAAGGAAAGCAC | 12 | 28 |
| HPV58 | TGACATTATGCACTGAAGT | 13 | 29 |
| HPV39 | TCCATACCTTCTAC | 15 | 30 |
| HPV51 | TTAGCACTGCCACTGCTGC | 16 | 31 |
| HPV56 | TTACTTAACTGTTCTGTAG | 17 | 32 |

Any one of the oligonucleotide sequences described herein may comprise, consist essentially of, or consist of a complement of any of the sequences disclosed herein. The terms "complement" or "complementary sequence," as used herein, refer to a nucleic acid sequence that forms a stable duplex with an oligonucleotide described herein via Watson-Crick base pairing rules, and typically shares about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% greater identity with the disclosed oligonucleotide. Nucleic acid sequence identity can be determined using any suitable mathematical algorithm or computer software known in the art, such as, for example, CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3×, FASTM, and SSEARCH) (for sequence alignment and sequence similarity searches). Sequence alignment algorithms also are disclosed in, for example, Altschul et al., *J. Molecular Biol.*, 215(3): 403-410 (1990); Beigert et al., *Proc. Natl. Acad Sci. USA*, 106(10): 3770-3775 (2009), Durbin et al., eds., *Biological Sequence Analysis: Probalistic Models of Proteins and Nucleic Acids*, Cambridge University Press, Cambridge, UK (2009); Soding, *Bioinformatics*, 21(7): 951-960 (2005); Altschul et al., *Nucleic Acids Res.*, 25(17): 3389-3402 (1997); and Gusfield, *Algorithms on Strings, Trees and Sequences*, Cambridge University Press, Cambridge UK (1997)).

The oligonucleotides described herein may be prepared using any suitable method, a variety of which are known in the art (see, for example, Sambrook et al., *Molecular Cloning. A Laboratory Manual*, 1989, 2. Supp. Ed., Cold Spring Harbour Laboratory Press: New York, N.Y.; M. A. Innis (Ed.), *PCR Protocols. A Guide to Methods and Applications*, Academic Press: New York, N.Y. (1990); P. Tijssen, *Hybridization with Nucleic Acid Probes—Laboratory Techniques in Biochemistry and Molecular Biology (Parts I and II)*, Elsevier Science (1993); M. A. Innis (Ed.), *PCR Strategies*, Academic Press: New York, N.Y. (1995); and F. M. Ausubel (Ed.), *Short Protocols in Molecular Biology*, John Wiley & Sons: Secaucus, N.J. (2002); Narang et al., *Meth. Enzymol.*, 68: 90-98 (1979); Brown et al., *Meth. Enzymol.*, 68: 109-151 (1979); and Belousov et al., *Nucleic Acids Res.*, 25: 3440-3444 (1997)). Primer pairs also can be designed using a variety of tools, such as the Primer-BLAST tool provided by the National Center of Biotechnology Information (NCBI). Oligonucleotide synthesis may be performed on oligo synthesizers such as those commercially available from Perkin Elmer/Applied Biosystems, Inc. (Foster City, Calif.), DuPont (Wilmington, Del.), or Milligen (Bedford, Mass.). Alternatively, oligonucleotides can be custom made and obtained from a variety of commercial sources well-known in the art, including, for example, the Midland Certified Reagent Company (Midland, Tex.), Eurofins Scientific (Louisville, Ky.), BioSearch Technologies, Inc. (Novato, Calif.), and the like. Oligonucleotides may be purified using any suitable method known in the art, such as, for example, native acrylamide gel electrophoresis, anion-exchange HPLC (see, e.g., Pearson et al., *J. Chrom.*, 255: 137-149 (1983)), and reverse phase HPLC (see, e.g., McFarland et al., *Nucleic Acids Res.*, 7: 1067-1080 (1979)).

The sequence of the primers and probes can be verified using any suitable sequencing method known in the art, including, but not limited to, chemical degradation (see, e.g., Maxam et al., *Methods of Enzymology*, 65: 499-560 (1980)), matrix-assisted laser desorption ionization time-of-flight (MALDI-TOF) mass spectrometry (see, e.g., Pieles et al., *Nucleic Acids Res.*, 21: 3191-3196 (1993)), mass spectrometry following a combination of alkaline phosphatase and exonuclease digestions (Wu et al., *Anal. Biochem.*, 290: 347-352 (2001)), and the like.

The primer and probe oligonucleotides described herein desirably comprise a melting temperature ($T_M$) in the range 45° C. to 80° C. In accordance with the present disclosure, the oligonucleotides specifically hybridize to a target HPV nucleic acid sequence without exhibiting significant hybridization to non-HPV nucleic acids. In addition, the oligonucleotides are selected such that they hybridize to conserved regions in the HPV genome, thus minimizing mismatches with the target sequence. This selection ensures that the oligonucleotides are capable of hybridizing to HPV nucleic acids from all genotypes and subtypes. Furthermore, the oligonucleotides are selected such that they show the least likelihood of dimer formation and contain minimal sequence repeats. Such properties can be determined by methods known in the art, for example, using the computer modelling program OLIGO® Primer Analysis Software (National Biosciences, Inc., Plymouth, Minn.).

Detectable Label

Any one or more of the primer and probe oligonucleotide sequences described herein may comprise a detectable label, such that the primer and/or probe can be visualized following binding to another entity (e.g., an amplification product or amplicon). In one embodiment, each of the probe oligonucleotide sequences described herein comprise a detectable label. The term "detectable label," as used herein, refers to a moiety or compound that generates a signal which can be measured and whose intensity is related to (e.g., proportional to) the amount of entity bound thereto. Any suitable detectable label that can be conjugated or linked to an oligonucleotide in order to detect binding of the oligonucleotide to a target sequence can be used, many of which are known in the art. In one embodiment, the detectable label may be detected indirectly. Indirectly detectable labels are typically specific binding members used in conjunction with a "conjugate" that is attached or coupled to a directly detectable label. Coupling chemistries for synthesizing such conjugates are well-known in the art and are designed such that the specific binding property of the specific binding member and the detectable property of the label remain intact. As used herein, "specific binding member" and "conjugate" refer to the two members of a binding pair, i.e. two different molecules, where the specific binding member binds specifically to the polynucleotide of the present disclosure, and the "conjugate" specifically binds to the specific binding member. Binding between the two members of the pair is typically chemical or physical in nature. Examples of such binding pairs include, but are not limited to, antigens and antibodies, avidin/streptavidin and biotin, haptens and antibodies specific for haptens, complementary nucleotide sequences, enzyme cofactors/substrates and enzymes, and the like.

In another embodiment, the detectable label may be directly detected. Such directly detectable labels include, for example, radioisotopes, fluorophores, chemiluminophores, enzymes, colloidal particles, fluorescent microparticles, intercalating dyes (e.g., SYBR Green or ethidium bromide), and the like. In one embodiment, the detectable label may be a fluorophore, such as a fluorescein-family dye, polyhalofluorescein-family dye, hexachlorofluorescein-family dye, coumarin-family dye, rhodamine-family dye, cyanine-family dye, oxazine-family dye, thiazin-family dye, squarainefamily dye, chelated lanthanide-family dye, azo-family dye, triphenylmethane-family dye, or a BODIPY®-family dye. Examples of fluorophores include, but are not limited to, FAM™, CAL-FLUOR®, QUASAR®, HEX™, JOE™, NED™, PET®, ROX™, TAMRA™, TET™, TEXAS RED®, and VIC®. One skilled in the art will appreciate that directly detectable labels may require additional components, such as substrates, triggering reagents, light, and the like, to enable detection of the label. Methods for labeling oligonucleotides, such as probes, are well-known in the art and described in, e.g., L. J. Kricka, *Ann. Clin. Biochem.*, 39: 114-129 (2002); van Gijlswijk et al., *Expert Rev. Mol. Diagn.*, 1: 81-91 (2001); Joos et al., *J. Biotechnol.*, 35: 135-153 (1994); Smith et al., *Nucl. Acids Res.*, 13: 2399-2412 (1985); Connoly et al., *Nucl. Acids Res.*, 13: 4485-4502 (1985); Broker et al., *Nucl. Acids Res.*, 5: 363-384 (1978); Bayer et al., *Methods of Biochem. Analysis*, 26: 1-45 (1980); Langer et al., *Proc. Natl. Acad. Sci. USA*, 78: 6633-6637 (1981); Richardson et al., *Nucl. Acids Res.*, 11: 6167-6184 (1983); Brigati et al., *Virol.*, 126: 32-50 (1983); Tchen et al., *Proc. Natl. Acad. Sci. USA*, 81: 3466-3470 (1984); Landegent et al., *Exp. Cell Res.*, 15: 61-72 (1984); A. H. Hopman et al., *Exp. Cell Res.*, 169: 357-368 (1987); and Temsamani et al., *Mol. Biotechnol.*, 5: 223-232 (1996).

In another embodiment, any one or more of the primer and probe oligonucleotide sequences described herein may also comprise a quencher moiety. When a detectable label (e.g., a fluorophore) and quencher moiety are held in close proximity, such as at the ends of a probe, the quencher moiety prevents detection of a signal (e.g., fluorescence) from the detectable label. When the two moieties are physically separated, such as after cleavage by a DNA polymerase, the signal becomes detectable. The quencher may be selected from any suitable quencher known in the art, such as, for example, BLACK HOLE QUENCHER® 1 (BHQ-1®), BLACK HOLE QUENCHER® 2 (BHQ-2®), IOWA BLACK® FQ, and IOWA BLACK® RQ. For example, the oligonucleotide probe may comprise a FAM fluorophore, CAL-FLUOR®, or QUASAR fluorophore and a BHQ-1 or BHQ-2 quencher.

Each of the probe oligonucleotide sequences desirably comprises a detectable label. Each of the probes may be labeled with the same detectable label or different detectable labels. In some embodiments, one group of two or more of the probe oligonucleotides described herein may comprise the same detectable label, forming a first label "group," while a second label "group" may be comprised of a group of two or more other probe oligonucleotides described herein, each comprising the same label but one that is different than the label of the first label group. For example, in one embodiment, (i) each of the first, second, and fifth probe oligonucleotide sequences described herein may comprise a different detectable label, (ii) each of the third, fourth, sixth, and seventh probe oligonucleotide sequences comprises the same detectable label, and/or (iii) each of the eighth through fifteenth probe oligonucleotides comprises the same detectable label, and the detectable labels of (i), (ii), and (iii) are different. In other embodiments, all of the probes described herein may comprise the same detectable label (e.g., FAM), such that amplification of the HPV target sequence is detected as a single signal during real-time PCR. When different detectable labels are employed, amplification of one or more HPV target sequences is detected as multiple separate signals, each corresponding to a particular label.

The selection of a particular labeling technique will depend on several factors, such as the ease and cost of the labeling method, spectral spacing between different detectable labels used, the quality of sample labeling desired, the effects of the detectable moiety on the hybridization reaction (e.g., on the rate and/or efficiency of the hybridization process), the nature of the amplification method used, the nature of the detection system, the nature and intensity of the signal generated by the detectable label, and the like.

Internal Control

The set of oligonucleotides for detecting HPV genotypes described above may further comprise primer and probe oligonucleotide sequences for amplifying and detecting an internal control (IC) sequence. In one embodiment, the internal control sequences are added to each sample preparation reaction. The internal control is then processed through the entire sample preparation and amplification procedure along with the test samples and calibrators (if present), to demonstrate proper sample processing and assay validity. The internal control may be any suitable non-HPV nucleic acid sequence, including, for example, a nucleic acid sequence encoding GAPDH, beta2-mciroglobulin, beta-actin, R18, or 16S RNA. In one embodiment, for example, the internal control comprises a DNA sequence derived or obtained from the human 3-globin gene. In this regard, the set of oligonucleotides described herein may further comprise an internal control forward primer oligonucleotide sequence comprising SEQ ID NO: 22 (5'-GTTGGTAT-CAAGGTTAC-3'), an internal control reverse primer oligonucleotide sequence comprising SEQ ID NO: 23 (5'-CCTAAGGGTGGGAAAATAGACC-3'), and an internal control probe oligonucleotide sequence comprising SEQ ID NO: 24 (5'-TTTCTGATAGGCACTGACTCTCTCTGCC-3'). The internal control probe desirably comprises a detectable label, such as any of those described herein. In one embodiment, the internal control probe may comprise a different label than the probes used to detect HPV, which allows for simultaneous detection and differentiation of internal control and HPV-amplified products within the same reaction. In one embodiment, the detectable label of the internal control probe oligonucleotide sequence is a coumarin-family dye, such as Coumarin47 (C47). The internal control probe may also comprise a quencher moiety, such as those described herein.

Method for Amplifying and Detecting Human Papilloma Virus

The present disclosure provides a method for detecting HPV of genotype 16, 18, 31, 33, 35, 39, 45, 51, 52, 56, 58, 59, 66, and/or 68 in a sample suspected of containing HPV. The method comprises: (a) contacting a sample obtained from a human with the set of oligonucleotide sequences described herein and reagents for amplification and detection of nucleic acid sequences, (b) amplifying one or more target HPV nucleic acid sequences present in the sample, (c) hybridizing one or more of the oligonucleotide probes to the one or more amplified target HPV nucleic acid sequences, (d) detecting hybridization of the one or more probe oligonucleotide sequences to the one or more amplified target HPV nucleic acid sequences by assessing a signal from each of the detectable labels, whereby (i) the presence of one or more signals indicates hybridization of the one or more probe oligonucleotide sequences to the one or more target HPV nucleic acid sequences and the presence of genotype 16, 18, 31, 33, 35, 39, 45, 51, 52, 56, 58, 59, 66, and/or 68 HPV in the sample, and (ii) the absence of signals indicates the absence of HPV in the sample. Descriptions of the primer and probe oligonucleotides set forth herein with respect to the aforementioned set of oligonucleotides also are applicable to those same aspects of the disclosed method.

A sample, as defined herein, is "suspected" of containing HPV of any one or combination of genotypes 16, 18, 31, 33, 35, 39, 45, 51, 52, 56, 58, 59, 66, and/or 68 if the sample is obtained from a subject, preferably a human, suspected of being infected with HPV. A subject is suspected of being infected with HPV if the subject has an increased risk for HPV. HPV risk factors include, but are not limited to, the number of sexual partners (e.g., more sexual partners increases HPV risk), age (e.g., children are at higher risk for common warts, while adolescents and young adults are a higher risk for genital warts), weakened immune systems, damaged skin, and personal contact (e.g., touching a wart).

The sample can be any suitable sample obtained from any suitable subject, typically a mammal (e.g., dogs, cats, rabbits, mice, rats, goats, sheep, cows, pigs, horses, non-human primates, or humans). Preferably, the subject is a human. The sample may be obtained from any biological source, such as, a cervical, vaginal, or anal swab or brush (e.g., via a Pap smear), or a physiological fluid including, but not limited to, whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and the like. In one embodiment, the sample is a cervical tissue specimen that has been extracted using any suitable collection method or system, such as, for example, the ALINITY m™ Cervi-Collect Specimen Collection Kit (Abbott Molecular, Abbott Park, Ill.) or THINPREP™ PreservCyt Solution (Hologic, Inc., Marlborough, Mass.). The sample can be obtained from the subject using routine techniques known to those skilled in the art, and the sample may be used directly as obtained from the biological source or following a pretreatment to modify the character of the sample. Such pretreatment may include, for example, preparing plasma from blood, diluting viscous fluids, filtration, precipitation, dilution, distillation, mixing, concentration, inactivation of interfering components, the addition of reagents, lysing, and the like.

After the sample is obtained from a subject, the sample may be contacted with the set of oligonucleotides comprising forward and reverse primers and probes as described herein to form a reaction mixture. The reaction mixture is then placed under amplification conditions. The term "amplification conditions," as used herein, refers to conditions that promote annealing and/or extension of primer sequences. Such conditions are well-known in the art and depend on the amplification method selected. For example, PCR amplification conditions generally comprise thermal cycling, e.g., cycling of the reaction mixture between two or more temperatures. Amplification conditions encompass all reaction conditions including, but not limited to, temperature and temperature cycling, buffer, salt, ionic strength, pH, and the like. The primers described herein hybridize to one or more target HPV nucleic acid sequences (e.g., the L1 gene of HPV genotype 16, 18, 31, 33, 35, 39, 45, 51, 52, 56, 58, 59, 66, and/or 68) if present in the sample, and any one or combination of target HPV nucleic acid sequences present in the sample is amplified.

Amplifying an HPV nucleic acid sequence in the sample can be performed using any suitable nucleic acid sequence amplification method known in the art, including but not limited to, polymerase chain reaction (PCR), reverse-transcriptase PCR (RT-PCR), real-time PCR, transcription-mediated amplification (TMA), rolling circle amplification, nucleic acid sequence-based amplification (NASBA), strand displacement amplification (SDA), and ligase chain reaction (LCR).

Amplification of HPV nucleic acid sequences desirably is performed using real-time PCR. "Real-time PCR," as used herein, refers to a PCR method in which the accumulation of amplification product is measured as the reaction progresses, in real time, with product quantification after each cycle, in contrast to conventional PCR in which the amplified DNA product is detected in an end-point analysis. Real-time PCR also is known in the art as "quantitative PCR (qPCR)." Real-time detection of PCR products typically involves the use of non-specific fluorescent dyes that intercalate with any double-stranded DNA and sequence-specific fluorescently-labeled DNA probes. Real-time PCR techniques and systems are known in the art (see, e.g., Dorak, M. Tevfik, ed. *Real-time PCR*. Taylor & Francis (2007); and Fraga et al., "Real-time PCR," *Current protocols essential laboratory techniques:* 10-3 (2008)) and are commercially available from a variety of sources (e.g., m2000rt REALTIME™ PCR system (Abbott Molecular, Inc., Des Plaines, Ill.); CFX Real-Time PCR Detection Systems (Bio-Rad Laboratories, Inc., Hercules, Calif.); and TAQMAN™ Real-Time PCR System (ThermoFisher Scientific, Waltham, Mass.)), any of which can be employed in the methods described herein.

Following amplification of one or more HPV virus nucleic acid sequences (e.g., the L1 gene of HPV genotype 16, 18, 31, 33, 35, 39, 45, 51, 52, 56, 58, 59, 66, and/or 68) that is present in the sample, the disclosed method further comprises hybridizing one or more of the probe oligonucleotide sequences disclosed herein to the one or more amplified target HPV nucleic acid sequences. In one embodiment, a reaction mixture comprising one or more HPV amplicons may be contacted with the probe oligonucleotide sequences disclosed herein that preferentially hybridize to a target nucleic acid sequence of the amplicon (or a complement thereof) in a genotype-specific manner under stringent hybridization and wash conditions, thereby forming one or more hybrid duplexes that are stable for detection.

"Hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. "Stringent hybridization conditions," as used herein, means conditions under which hybridization of fully complementary nucleic acid strands is strongly preferred. Under stringent hybridization conditions, a first nucleic acid sequence (for example, a primer) will hybridize to a second nucleic acid sequence (for example, a target sequence), such as in a complex mixture of nucleic acids. Stringent conditions are sequence-dependent and will be different in different circumstances. Stringent conditions can be selected to be about 5-10° C. lower than the thermal melting point ($T_m$) for the specific sequence at a defined ionic strength pH. The $T_m$ can be the temperature (under defined ionic strength, pH, and nucleic concentration) at which 50% of an oligonucleotide complementary to a target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C. Any suitable method and conditions for hybridizing oligonucleotide probes to target HPV nucleic acid sequences known in the art can be used in the disclosed method.

Following hybridization of the one or more of the probe oligonucleotide sequences to the one or more amplified target HPV nucleic acid sequences, the method comprises detecting hybridization of the one or more probe oligonucleotide sequences to the one or more amplified target HPV nucleic acid sequences by assessing a signal from each of the detectable labels, whereby (i) the presence of one or more signals indicates hybridization of the one or more probe oligonucleotide sequences to the one or more target HPV nucleic acid sequences and the presence of genotype 16, 18, 31, 33, 35, 39, 45, 51, 52, 56, 58, 59, 66, and/or 68 HPV in the sample, and (ii) the absence of signals indicates the absence of HPV in the sample. Detection of signals from the one or more probe oligonucleotide sequences may be performed using a variety of well-known methodologies, including, for example homogeneous or heterogeneous techniques.

Homogeneous detection methods involve detecting products of the amplification reaction as they are formed, namely, in a real time manner. As a result, amplification product/probe hybrids are formed and detected while the reaction mixture is under amplification conditions. Homogeneous detection methods include, but are not limited to, the use of FRET labels that are attached to the probes and that emit a signal in the presence of the target sequence, Molecular Beacons (See, Tyagi et al., *Nature Biotechnol.*, 14: 303-308 (1996); Tyagi et al., *Nature Biotechnol.*, 16: 49-53 (1998); Kostrikis et al., *Science*, 279: 1228-1229 (1998); Sokol et al., *Proc. Natl. Acad. Sci. USA*, 95: 11538-11543 (1998); Marras et al., *Genet. Anal.*, 14: 151-156 (1999); and U.S. Pat. Nos. 5,846,726, 5,925,517, 6,277,581 and 6,235,504), TAQMAN® assays (see, e.g., U.S. Pat. Nos. 5,210,015; 5,804,375; 5,487,792 and 6,214,979 and International Patent Application Publication WO 01/86001), and hybridization protection assays (HPA) which utilize probes labeled with acridinium ester (AE) (see, e.g., Weeks et al., *Clin. Chem.*, 29: 1474-1479 (1983); Berry et al., *Clin. Chem.*, 34: 2087-2090 (1988)).

Heterogeneous detection systems generally employ a capture agent to separate amplified sequences from other materials in the reaction mixture. Capture agents typically comprise a solid support material (e.g., microtiter wells, beads, chips, and the like) coated with one or more specific binding sequences. A binding sequence may be complementary to a tail sequence added to oligonucleotide probes of the disclosure. Alternatively, a binding sequence may be complementary to a sequence of a capture oligonucleotide, itself comprising a sequence complementary to a tail sequence of a probe. After separation of the amplification product/probe hybrids bound to the capture agents from the remaining reaction mixture, the amplification product/probe hybrids can be detected using any suitable detection method known in the art or described herein.

Kits for Amplifying and Detecting a Human Papilloma Virus Nucleic Acid Sequence

The disclosure also provides a kit for amplifying and detecting human HPV of genotype 16, 18, 31, 33, 35, 39, 45, 51, 52, 56, 58, 59, 66, and/or 68 in a sample. The kit comprises (a) forward primer oligonucleotide sequences comprising SEQ ID NO: 1, SEQ ID NO: 2, SEQ ID NO: 3, and SEQ ID NO: 4; (b) reverse primer oligonucleotide sequences comprising SEQ ID NO: 5 and SEQ ID NO: 6; (c) a first probe oligonucleotide sequence comprising SEQ ID NO: 7 which specifically hybridizes to HPV genotype 16; (d) a second probe oligonucleotide sequence comprising SEQ ID NO: 8 which specifically hybridizes to HPV genotype 18; (e) a third probe oligonucleotide sequence comprising SEQ ID NO: 9 which specifically hybridizes to HPV genotype 31; (f) a fourth probe oligonucleotide sequence comprising SEQ ID NO: 10 which specifically hybridizes to HPV genotype 33; (g) a fifth probe oligonucleotide sequence comprising SEQ ID NO: 11 which specifically hybridizes to HPV genotype 45; (h) a sixth probe oligonucleotide sequence comprising SEQ ID NO: 12 which specifically hybridizes to HPV genotype 52; (i) a seventh probe oligonucleotide sequence comprising SEQ ID NO: 13 which specifically hybridizes to HPV genotype 58; (j) an eighth probe oligonucleotide sequence comprising SEQ ID NO: 14 which specifically hybridizes to HPV genotype 35; (k) a ninth probe oligonucleotide sequence comprising SEQ ID NO: 15 which specifically hybridizes to HPV genotype 39; (l) a tenth probe oligonucleotide sequence comprising SEQ ID NO: 16 which specifically hybridizes to HPV genotype 51; (m) an eleventh probe oligonucleotide sequence comprising SEQ ID NO: 17 which specifically hybridizes to HPV genotype 56; (n) a twelfth probe oligonucleotide sequence comprising SEQ ID NO: 18 which specifically hybridizes to HPV genotype 59; (o) a thirteenth probe oligonucleotide sequence comprising SEQ ID NO: 19 which specifically hybridizes to HPV genotype 66; (p) a fourteenth probe oligonucleotide sequence comprising SEQ ID NO: 20 which specifically hybridizes to HPV genotype 68a; (q) a fifteenth probe oligonucleotide sequence comprising SEQ ID NO: 21 which specifically hybridizes to HPV genotype 68b, wherein each of the probe oligonucleotide sequences of (c)-(q) comprises a detectable label. The kit further comprises reagents for amplifying and detecting nucleic acid sequences, and instructions for amplifying and detecting HPV. Descriptions of the primer oligonucleotides and probe oligonucleotides set forth herein with respect to the aforementioned methods also are applicable to those same aspects of the kit described herein. Examples of suitable reagents for inclusion in the kit (in addition to the oligonucleotide primers and probes described herein) include conventional reagents employed in nucleic acid amplification reactions, such as, for example, one or more enzymes having polymerase activity, enzyme cofactors (such as magnesium or nicotinamide adenine dinucleotide (NAD)), salts, buffers, deoxyribonucleotide, or ribonucleotide triphosphates (dNTPs/rNTPs; for example, deoxyadenosine triphosphate, deoxyguanosine triphosphate, deoxycytidine triphosphate, and deoxythymidine triphosphate) blocking agents, labeling agents, and the like. Many such reagents are described herein or otherwise known in the art and commercially available.

The kit may comprise instructions for using the amplification reagents and primer and probe oligonucleotides described herein, e.g., for processing the test sample, extracting nucleic acid molecules, and/or performing the test; and for interpreting the results obtained, as well as a notice in the form prescribed by a governmental agency. Such instructions optionally can be in printed form or on CD, DVD, or other format of recorded media.

The aforementioned kit may further comprise primer and probe oligonucleotides that amplify and detect an internal control nucleic acid sequence, such as a human β-globin gene, as described herein. In this regard, the kit and/or composition may comprise an internal control forward primer oligonucleotide sequence comprising SEQ ID NO: 22, an internal control reverse primer oligonucleotide sequence comprising SEQ ID NO: 23, and an internal control probe oligonucleotide sequence comprising SEQ ID NO: 24 which comprises a detectable label.

The kit may be supplied in a solid (e.g., lyophilized) or liquid form. In one embodiment, the primer oligonucleotides, probe oligonucleotides, and other reagents are lyophilized (i.e., freeze dried). The various components of the kit of the present disclosure may optionally be contained within different containers (e.g., vial, ampoule, test tube, flask, or bottle) for each individual component (e.g., primer oligonucleotides, probe oligonucleotides, or buffer). Each component will generally be suitable as aliquoted in its respective container or provided in a concentrated form. Other containers suitable for conducting certain steps of the amplification/detection assay may also be provided. The individual containers are preferably maintained in close confinement for commercial sale.

The following examples further illustrate the invention but, of course, should not be construed as in any way limiting its scope.

Example 1

This example demonstrates a method for amplifying and detecting HPV in a sample in accordance with the present disclosure.

An HPV detection assay that utilizes real-time RT-PCR to amplify and detect high-risk HPV genotypes 16, 18, 31, 33, 35, 39, 45, 51, 52, 56, 58, 59, 66, and/or 68 extracted from human cervical specimens has been developed by Abbott Molecular, Inc. (Abbott Park, Ill.) under the brand name ALINITY m™ HR HPV Assay. The Alinity m™ HR HPV assay is intended for the following uses: (1) to screen patients with ASC-US (atypical squamous cells of undetermined significance) cervical cytology test results to determine the need for referral to colposcopy; (2) to be used with cervical cytology to adjunctively screen to assess the presence or absence of high-risk HPV genotype; (3) to be used as a first-line primary screening test to identify women at increased risk for the development of cervical cancer or the presence of high-grade disease; (4) to assess the presence or absence of HPV genotypes 16 and 18 to identify women at increased risk for the development of cervical cancer or the presence of high-grade disease with or without cervical cytology.

The ALINITY m™ HR HPV assay consists of sample preparation, PCR assembly, amplification/detection, and result calculation and reporting. All stages of the ALINITY m™ HR HPV assay procedure are executed automatically by the ALINITY m™ instrument. The ALINITY m™ System is designed to be a random-access analyzer that can perform the ALINITY m™ HR HPV assay in parallel with other ALINITY m™ assays on the same instrument.

Nucleic acids from specimens are is extracted using the ALINITY m™ Sample Prep Kit, ALINITY m™ Lysis Solution, ALINITY m™ Ethanol Solution, and ALINITY m™ Diluent Solution. The ALINITY m™ System employs magnetic microparticle technology to facilitate nucleic acid capture, wash, and elution.

The resulting purified nucleic acids are then combined with a liquid unit-dose activator reagent, lyophilized unit-dose ALINITY m™ HR HPV amplification/detection reagents (including PCR master mix) and transferred into a reaction vessel. ALINITY m™ Vapor Barrier Solution (mineral oil) is then added to the reaction vessel which is then transferred to an amplification/detection unit for PCR amplification and real-time fluorescence detection of HR HPV and endogenous human beta globin (BG).

The primer oligonucleotide sequences are set forth in Table 2, and the probe oligonucleotide sequences are set forth in Table 3.

TABLE 2

| Primer Sequences for ALINITY M™ HR HPV ASSAY | | |
|---|---|---|
| Oligo Sequence Name | Sequence 5'-3' | SEQ ID NO |
| HPV PCR Forward Primer 1 | TATTTGTTACTGTGGTAGATACTAC | 1 |
| HPV PCR Forward Primer 2 | CAATTGTTTGTTACTGTTGTGGATACTAC | 2 |
| HPV PCR Forward Primer 3 | TTTTTATTACCTGTGTTGATACTAC | 3 |
| HPV fp16-25 | TATTTGTTACTGTTGTTGATACTAC | 4 |
| HPV PCR Reverse Primer | GAAAAATAAACTGTAAATCATATTCCTC | 5 |
| HPV rp35-35 | TGAAAAATAAACTGTAAATCATATTCTTCACCATG | 6 |

TABLE 3

Probe Sequences for ALINITY M™ HR HPV ASSAY

| Oligo Sequence Name | Sequence Propyne-modified nucleotides indicated in bold | Non-Propyne Modified SEQ ID NO | Propyne Modified SEQ ID NO |
|---|---|---|---|
| C560-HPV16+Pb-20a | 5'-0560-CTGCCATATCTACTTCAGAA-BHQ1-dT-3' | 7 | 25 |
| C610-HPV18Pb-22 | 5'-C610-CACAGTCTCCTGTACCTGGGCA-BHQ2-dT-3' | 8 | N/A |
| Q670-HPV31+Pb-20 | 5'-Q670-AAGTAGTAATTTTAAAGAGT-BHQ2-dT-3' | 9 | 26 |
| Q670-HPV33+Pb-19 | 5'-Q670-ATGCACACAAGTAACTAGT-BHQ2-dT-3' | 10 | 27 |
| Q670-HPV45Pb-22 | 5'-Q670-CCTACTAAGTTTAAGCAGTATA-BHQ2-dT-3' | 11 | N/A |
| Q705-HPV52+Pb-14 | 5'-Q705-AAAAAGGAAAGCAC-BHQ2-dT-3' | 12 | 28 |
| Q705-HPV58+Pb-19 | 5'-Q705-TGACATTATGCACTGAAGT-BHQ2-dT-3' | 13 | 29 |
| FAM-HPV35 PCR Probe | 5'-6FAM-CTGTGTGTTCTGCTGTGTC-BHQ1-dT-3' | 14 | N/A |
| FAM-HPV39 PCR Probe | 5'-6FAM-TCCATACCTTCTAC-BHQ1-dT-3' | 15 | 30 |
| FAM-HPV51+Pb-19 | 5'-6FAM-TTAGCACTGCCACTGCTGC-BHQ1-dT-3' | 16 | 31 |
| FAM-rHPV56+Pb-19 | 5'-6FAM-TTACTTAACTGTTCTGTAG-BHQ1-dT-3' | 17 | 32 |
| FAM-HPV59 PCR Probe | 5'-6FAM-ATTCCTAATGTATACACACCTACC-BHQ1-dT-3' | 18 | N/A |
| FAM-HPV66 PCR Probe | 5'-6FAM-CAATCAATACCTTCGCCATGTG-BHQ1-dT-3' | 19 | N/A |
| FAM-HPV68 PCR Probe (68b) | 5'-6FAM-CTTTGTCTACTACTACTGA-BHQ1-dT-3' | 20 | N/A |
| FAM-HPV68aPb | 5'-6FAM-CATTGTCCACTACTACAGA-BHQ1-dT-3' | 21 | N/A |

The PCR master mix reagent formulation is compatible with lyophilization and enables rapid PCR (i.e., completion of cycling in less than one hour). Master mix reagent is prepared by combining oligonucleotide primers, oligonucleotide probes, dNTPs, PCR buffer components (Tris-HCl, Tween-20, and Fish Gelatin), KAPA2G Fast DNA Polymerase, Uracil-DNA Glycosylase (UDG), excipient (Ficoll 400, Ficoll 70, Melezitose, Trehalose), and Molecular Biology Grade Water. KAPA2G Fast DNA Polymerase is an engineered enzyme for higher processivity and speed through directed evolution, which exhibits significantly faster extension rates than wild-type Taq DNA polymerase. It has a highly processive 5'-3' DNA polymerase but lacks 3'-5' exonuclease activity. Uracil-DNA Glycosylase (UDG) catalyzes the release of free uracil from uracil-containing DNA and provides a means of contamination control for external amplicons containing uracil. The master mix reagent is filled in unit-dose format into multi-well plates and lyophilized. The lyophilized plates are then sealed and pouched. The formulation of the PCR master mix reagent is shown in Table 4.

TABLE 4

PCR Master Mix Reagent Formulation

| Component | HPV AMP TRAY 1 MMx/Well Reagent Component Concentration |
|---|---|
| HPV PCR Forward Primer 1 | 0.250 μM |
| HPV PCR Forward Primer 2 | 0.250 μM |
| HPV PCR Forward Primer 3 | 0.250 μM |
| HPV fp16-25 | 0.250 μM |
| HPV PCR Reverse Primer 1 | 0.375 μM |
| HPV rp35-35 | 0.375 μM |
| HPV IC FP-17 | 0.150 μM |
| HPV IC Reverse Primer | 0.175 μM |
| C560-HPV16 + Pb-20a | 0.040 μM |
| C610-HPV18Pb-22 | 0.030 μM |
| Q705-HPV45Pb-22 | 0.030 μM |
| Q670-HPV31 + Pb-20 | 0.022 μM |
| Q670-HPV33 + Pb-19 | 0.020 μM |
| Q670-HPV52 + Pb-14 | 0.030 μM |
| Q670-HPV58 + Pb-19 | 0.030 μM |
| FAM-HPV35 PCR Probe | 0.025 μM |
| FAM-HPV39 PCR Probe | 0.025 μM |
| FAM-HPV51 + Pb-19 | 0.020 μM |
| FAM-rHPV56 + Pb-19 | 0.018 μM |
| FAM-HPV59 PCR Probe | 0.022 μM |
| FAM-HPV66 PCR Probe | 0.020 μM |
| FAM-HPV68 PCR Probe (68b) | 0.030 μM |
| FAM-HPV68aPb | 0.030 μM |
| C47-HPV IC Pb-28 | 0.018 μM |
| dNTPs | 0.85 mM |
| Tris-HCl | 50 mM |
| Tween-20 | 0.01% (V/V) |
| Fish Gelatin | 0.01% (W/V) |
| Fast Enzyme (KAPA2G Fast DNA Polymerase) | 1.75 units |
| Uracil-DNA Glycosylase (UDG) | 0.25 units |
| Ficoll400 | 15% (W/V) |
| Ficoll70 | 15% (W/V) |
| Melezitose | 5% (W/V) |
| Trehalose | 15% (W/V) |
| Molecular Biology Grade Water | N/A |

The activator solution is prepared by mixing molecular biology grade water, magnesium chloride, tetramethyl ammonium chloride (TMAC), potassium chloride, and ProClin 950. The activator solution is supplied in liquid format in sealed and pouched multi-well plates and provides the PCR reaction with the necessary salts to activate PCR Fast enzyme and establish an optimal ionic strength environment. The formulation of the activator solution is shown in Table 5.

TABLE 5

Activator Reagent Formulation

| Component | Concentration/Well |
|---|---|
| Magnesium Chloride (MgCl$_2$) | 8.5 mM |
| Tetramethyl Ammonium Chloride (TMAC) | 60 mM |
| Potassium chloride (KCl) | 60 mM |
| ProClin 950 | 0.15% (V/V) |
| Molecular Biology Grade Water | N/A |

The PCR cycling conditions used by the ALINITY m™ HR HPV assay are set forth in Table 6.

TABLE 6

PCR Cycling Conditions

| Stage | Step | Temp (° C.) | Duration (seconds) | Number of Cycles | Read? (0 = No read) (1 = Read) | Overshoot Temp (° C.) | Overshoot Duration (seconds) | Ramp Rate (° C./second) |
|---|---|---|---|---|---|---|---|---|
| 1 | 1 | 46.4 | 255.99 | 1 | 0 | 0 | 0 | 10 |
|   | 2 | 96.9 | 195.74 | 1 | 0 | 801 | 7.7 | 10 |
| 2 | 1 | 96.9 | 3 | 4 | 0 | 801 | 7.1 | 10 |
|   | 2 | 51.6 | 20 | 4 | 0 | 10 | 4.6 | 8 |
| 3 | 1 | 96.9 | 3 | 36 | 0 | 801 | 7 | 10 |
|   | 2 | 51.6 | 20 | 36 | 0 | 10 | 4.6 | 8 |
|   | 3 | 54.7 | 15.68 | 36 | 1 | 5 | 3.5 | 10 |

The PCR formulation and cycling conditions described above may be further modified to optimize the assay.

Example 2

This example describes the clinical sensitivity and specificity of the HPV detection method disclosed herein for detecting cervical disease.

The clinical sensitivity and specificity for detection of cervical disease (referred to as "≥CIN2") among a screening population (age ≥30 years) were determined for the ALINITY m™ HR HPV assay described herein in comparison with hc2 High-Risk HPV DNA Test (hc2) and Abbott REALTIME™ High Risk (HR) HPV. All specimens were collected in THINPREP PRESERVCYT™ Solution. The results are shown in Table 7.

TABLE 7

Clinical Sensitivity and Specificity in Screening Population

| | Sensitivity (%) | | Specificity (%) | |
|---|---|---|---|---|
| Assay | Estimate (95% CI) | n/N[a] | Estimate (95% CI) | n/N[b] |
| ALINITY m HR HPV | 100.0 (94.7, 100.0) | 68/68 | 93.2 (92.2, 94.0) | 2768/2971 |
| hc2 | 95.6 (87.8, 98.5) | 65/68 | 92.9 (91.9, 93.7) | 2759/2971 |
| Abbott RealTime HR HPV | 100.0 (94.7, 100.0) | 68/68 | 94.2 (93.3, 95.0) | 2794/2967 |

[a]n represents the number of ≥CIN2 specimens detected. N represents the number of ≥CIN2 specimens tested.
[b]n represents the number of disease negative specimens that were not detected. N represents the number of disease negative specimens that were tested. Negative disease status is defined as either <CIN2 histology or negative cytology when histology result was unknown.

Among the 68≥CIN2 specimens, 34 were ≥CIN3. The clinical sensitivity for detection of ≥CIN3 was 100.0% (34/34; 95% CI 89.8% to 100.0%) for ALINITY m™ HR HPV, 97.1% (33/34; 95% CI 85.1% to 99.5%) for hc2, and 100.0% (34/34; 95% CI 89.8% to 100.0%) for Abbott REALTIME™ HR HPV.

Example 3

This example describes the clinical sensitivity of the HPV detection method disclosed herein for detecting cervical disease in patients with ASC-US cytology.

ASC-US, also referred to as atypical squamous cells of undetermined significance, is the most common abnormal finding in a Pap test. It may be a sign of infection with certain types of human papillomavirus (HPV) or a benign growth. The clinical sensitivity for detection of ≥CIN2 among patients with ASC-US cytology were determined for the ALINITY m™ HR HPV assay described herein in comparison with hc2 High-Risk HPV DNA Test (hc2) and Abbott REALTIME™ High Risk (HR) HPV. All specimens were collected in THINPREP PRESERVCYT™ Solution. The results are shown in Table 8.

TABLE 8

Clinical Sensitivity in ASC-US Population

| Assay | Estimate (95% CI) | n/N[a] |
|---|---|---|
| ALINITY m HR HPV | 96.8 (83.8, 99.4) | 30/31 |
| hc2 | 93.5 (79.3, 98.2) | 29/31 |
| Abbott RealTime HR HPV | 96.8 (83.8, 99.4) | 30/31 |

[a]n represents the number of ≥CIN2 specimens detected. N represents the number of ≥CIN2 specimens tested.

Example 4

This example describes the clinical specificity of the HPV detection method disclosed herein in a screening population with normal cytology.

The clinical specificity in a screening population (age ≥30 years) with normal cytology was determined for ALINITY m™ HR HPV assay described herein in comparison with hc2 High-Risk HPV DNA Test (hc2) and Abbott REALTIME™ High Risk (HR) HPV. All specimens were collected in THINPREP PRESERVCYT™ Solution. The results are shown in Table 9.

TABLE 9

Clinical Specificity in Screening Population with Normal Cytology

| Assay | Estimate (95% CI) | n/N[a] |
|---|---|---|
| ALINITY m HR HPV | 92.8 (91.8, 93.7) | 2762/2976 |
| hc2 | 92.5 (91.5, 93.4) | 2753/2976 |
| Abbott RealTime HR HPV | 93.8 (92.9, 94.6) | 2788/2972 |

[a]n represents the number of specimens that were not detected. N represents the number of specimens tested.

Example 5

This example describes the accuracy or the HPV detection method disclosed herein in for identifying HPV 16 and/or HPV 18 in women with cervical disease.

The performance of the ALINITY m™ HR HPV assay in identification of HPV 16 and/or HPV 18 in ≥CIN2 was evaluated based on the results from a screening population (age ≥30 years), as shown in Table 10, and an ASC-US population, as shown in Table 11. Out of 68≥CIN2 specimens from the screening population, 68 had an interpretation of "HR HPV Detected" from both ALINITY m™ HR HPV and Abbott REALTIME™ HR HPV. Thirty-five specimens were detected as HPV 16 and/or HPV 18 by both assays. Thirty-three specimens were detected as non-HPV 16/18 by both assays. The overall agreement for detection of HPV 16 and/or HPV 18 between ALINITY m™ HR HPV and Abbott REALTIME™ HR HPV was 100.0% (68/68).

TABLE 10

Genotyping Accuracy for HPV 16 and/or HPV 18 in Screening Population

| | Abbott REALTIME ™ HR HPV | |
|---|---|---|
| ALINITY m HR HPV | HPV 16 and/or HPV 18 Detected[a] | Non-HPV 16/18 High Risk Genotype(s) Detected[b] |
| HPV 16 and/or HPV 18 Detected[a] | 35 | 0 |
| Non-HPV 16/18 High Risk Genotype(s) Detected[b] | 0 | 33 |

[a]These specimens were detected for HPV 16 and/or HPV 18 signal(s) with or without non-HPV 16/18 HR HPV signal detected.
[b]These specimens were not detected for HPV 16 or HPV 18 signal and detected for non-HPV 16/18 HR HPV signal.

Out of 31≥CIN2 specimens from the ASC-US population, 30 had an interpretation of "HR HPV Detected" from both ALINITY m™ HR HPV and Abbott REALTIME™ HR HPV, as shown in Table 11. Twenty two specimens were detected as HPV 16 and/or HPV 18 by both assays. Eight specimens were detected as non-HPV 16/18 by both assays. The overall agreement for detection of HPV 16 and/or HPV 18 between ALINITY m™ HR HPV and Abbott REALTIME™ HR HPV was 100.0% (30/30).

TABLE 11

Genotyping Accuracy for HPV 16 and/or HPV 18 in ASC-US Population

| | Abbott REALTIME ™ HR HPV | |
|---|---|---|
| ALINITY m HR HPV | HPV 16 and/or HPV 18 Detected[a] | Non-HPV 16/18 High Risk Genotype(s) Detected[b] |
| HPV 16 and/or HPV 18 Detected[a] | 22 | 0 |
| Non-HPV 16/18 High Risk Genotype(s) Detected[b] | 0 | 8 |

[a]These specimens were detected for HPV 16 and/or HPV 18 signal(s) with or without non-HPV 16/18 HR HPV signal detected.
[b]These specimens were not detected for HPV 16 or HPV 18 signal and detected for non-HPV 16/18 HR HPV signal.

Example 6

This example demonstrates the use of the ALINITY m™ HR HPV assay to estimate relative disease risk associated with different genotype results.

The relative risks of having cervical disease (≥CIN2) were estimated by calculating the ratio of absolute risks, for HPV 16 and/or HPV 18 Detected vs. Non-HPV 16/18 HR HPV Detected results in a screening population (age ≥30 years) and an ASC-US Population. The relative risk was 2.3 in screening population, and 2.1 in ASC-US population, as shown in Table 12.

TABLE 12

Relative Risk of Cervical Disease Associated with Different Genotype Results (HPV 16 and/or HPV 18 Detected vs Non-HPV 16/18 HR HPV Detected)

| Population | Relative Risk | 95% CI |
|---|---|---|
| Screening | 2.3 | (1.6, 3.5) |
| ASC-US | 2.1 | (1.1, 4.1) |

Example 7

This example demonstrates the ability of the ALINITY m™ HR HPV assay to detect multiple HPV genotypes.

The ability of ALINITY m HR HPV to detect 14 HR HPV genotypes (HPV 16, 18, 31, 33, 35, 39, 45, 51, 52, 56, 58, 59, 66, and 68) and to specifically identify HPV genotypes 16, 18 and 45 while reporting the concurrent detection of the other high-risk genotypes (Other HR HPV A: 31/33/52/58; Other HR HPV B: 35/39/51/56/59/66/68) was evaluated. Forty samples containing HPV DNA targets from 14 genotypes, individually and in combinations, were tested as listed in Table 13. Results from all samples including 14 with single genotype, 10 with 2 genotypes, 10 with 3 genotypes, 5 with 4 genotypes and 1 with 5 genotypes were reported accurately. The presence or absence of HPV DNA for each designated signal, HPV 16, HPV 18, HPV 45, other HR HPV A and other HR HPV B, was accurately determined in each case.

TABLE 13

Genotype Detection and Partial Genotyping Capability

| Sample No. | Genotypes(s) | Reported Result |
|---|---|---|
| 1 | HPV 16 | HPV 16 |
| 2 | HPV 18 | HPV 18 |
| 3 | HPV 31 | Other HR HPV A |
| 4 | HPV 33 | Other HR HPV A |
| 5 | HPV 35 | Other HR HPV B |
| 6 | HPV 39 | Other HR HPV B |
| 7 | HPV 45 | HPV 45 |
| 8 | HPV 51 | Other HR HPV B |
| 9 | HPV 52 | Other HR HPV A |
| 10 | HPV 56 | Other HR HPV B |
| 11 | HPV 58 | Other HR HPV A |
| 12 | HPV 59 | Other HR HPV B |
| 13 | HPV 66 | Other HR HPV B |
| 14 | HPV 68 | Other HR HPV B |
| 15 | HPV 16 and HPV 18 | HPV 16; HPV 18 |
| 16 | HPV 16 and HPV 45 | HPV 16; HPV 45 |
| 17 | HPV 16 and HPV 58 | HPV 16; Other HR HPV A |
| 18 | HPV 16 and HPV 39 | HPV 16; Other HR HPV B |
| 19 | HPV 18 and HPV 45 | HPV 18; HPV 45 |
| 20 | HPV 18 and HPV 58 | HPV 18; Other HR HPV A |
| 21 | HPV 18 and HPV 39 | HPV 18; Other HR HPV B |
| 22 | HPV 45 and HPV 58 | HPV 45; Other HR HPV A |
| 23 | HPV 45 and HPV 39 | HBV 45; Other HR HPV B |
| 24 | HPV 58 and HPV 39 | Other HR HPV A; Other HR HPV B |
| 25 | HPV 16, HPV 18, and HPV 45 | HPV 16; HPV 18; HPV 45 |
| 26 | HPV 16, HPV 18, and HPV 58 | HPV 16; HPV 18; Other HR HPV A |
| 27 | HPV 16, HPV 18, and HPV 39 | HPV 16; HPV 18; Other HR HPV B |
| 28 | HPV 16, HPV 45, and HPV 58 | HPV 16; HPV 45; Other HR HPV A |
| 29 | HPV 16, HPV 45, and HPV 39 | HPV 16; HPV 45; Other HR HPV B |
| 30 | HPV 16, HPV 58, and HPV 39 | HPV 16; Other HR HPV A; Other HR HPV B |
| 31 | HPV 18, HPV 45, and HPV 58 | HPV 18; HPV 45; Other HR HPV A |
| 32 | HPV 18, HPV 45, and HPV 39 | HPV 18; HPV 45; Other HR HPV B |
| 33 | HPV 18, HPV 58, and HPV 39 | HPV 18; Other HR HPV A; Other HR HPV B |
| 34 | HPV 45, HPV 58, and HPV 39 | HPV 45; Other HR HPV A; Other HR HPV B |
| 35 | HPV 16, HPV 18, HPV 45, and HPV 58 | HPV 16; HPV 18; HPV 45; Other HR HPV A |
| 36 | HPV 16, HPV 18, HPV 45, and HPV 39 | HPV 16; HPV 18; HPV 45; Other HR HPV B |
| 37 | HPV 16, HPV 18, HPV 58, and HPV 39 | HPV 16; HPV 18; Other HR HPV A; Other HR HPV B |
| 38 | HPV 16, HPV 45, HPV 58, and HPV 39 | HPV 16; HPV 45; Other HR HPV A; Other HR HPV B |
| 39 | HPV 18, HPV 45, HPV 58, and HPV 39 | HPV 18; HPV 45; Other HR HPV A; Other HR HPV B |
| 40 | HPV 16, HPV 18, HPV 45, HPV 58, and HPV 39 | HPV 16; HPV 18; HPV 45; Other HR HPV A; Other HR HPV B |

Example 8

This example demonstrates the determination of the limit of detection (LOD) of the ALINITY m™ HR HPV assay.

Limit of detection (LOD) of ALINITY m™ HR HPV was determined by testing plasmids for 14 HR HPV genotype sequences (16, 18, 31, 33, 35, 39, 45, 51, 52, 56, 58, 59, 66, and 68) in THINPREP PRESERVCYT™ solution containing an HPV negative human cell line (C33A) background. In addition, LOD was determined by testing HPV positive cell lines, SiHa (HPV 16) and HeLa (HPV18), in PRESERVCYT™ solution containing a C33A cell line background. Four hundred microliters of sample was used per assay. Each plasmid or cell line was diluted to 4 concentrations, including at, below, and above the expected LOD levels, and was tested with 2 lots of amplification reagents. For each plasmid or cell line, a total of 72 replicates were tested across all concentrations (i.e., 4 concentrations, 6 replicates per day over 3 days per concentration) with each amplification reagent lot. The LOD was defined as a concentration having a ≥95% detection rate with all higher concentrations having a ≥95% detection rate. The LOD was 40 cells per assay for SiHa (HPV 16) and HeLa (HPV 18); 240 copies per assay for HPV 16 and 18; 500 copies per assay for HPV 45; 2000 copies per assay for HPV 33, 35, 51, 52, and 59; and 5000 copies per assay for HPV 31, 39, 56, 58, 66 and 68.

Example 9

This example demonstrates the reproducibility of the ALINITY m™ HR HPV assay.

A total of 581 specimens were tested to evaluate the reproducibility of ALINITY m HR HPV within the same laboratory. Each of the specimens was tested twice by two operators in the same laboratory. As shown in Table 14, the overall percent agreement between the two tests was 97.9% (569/581; 95% CI: 96.4% to 98.8%), with an average positive agreement of 96.9% (370/382; 95% CI: 94.9% to 98.5%) and an average negative agreement of 98.5% (768/780; 95% CI: 97.5% to 99.2%).

TABLE 14

Intra-Laboratory Reproducibility

|  |  | Second Test | |
| --- | --- | --- | --- |
|  |  | HR HPV Detected | Not Detected |
| First Test | HR HPV Detected | 185 | 5 |
|  | Not Detected | 7 | 384 |

A total of 560 specimens were tested to evaluate the reproducibility of ALINITY m™ HR HPV between two laboratories at Abbott using different ALINITY m™ Systems. As shown in Table 15, the overall percent agreement between the two tests was 97.5% (546/560; 95% CI: 95.8% to 98.5%), with an average positive agreement of 96.1% (342/356; 95% CI: 93.7% to 97.9%) and an average negative agreement of 98.2% (750/764; 95% CI: 97.1% to 99.0%).

TABLE 15

Inter-Laboratory Reproducibility

|  |  | Second Laboratory | |
| --- | --- | --- | --- |
|  |  | HR HPV Detected | Not Detected |
| First Laboratory | HR HPV Detected | 171 | 9 |
|  | Not Detected | 5 | 375 |

Example 10

This example demonstrates the analytical specificity of the ALINITY m™ HR HPV assay.

The analytical specificity of ALINITY m™ HR HPV was evaluated with a panel of microorganisms (see Table 16) in HPV negative samples and HR HPV positive samples (containing HPV at 3 times the limit of detection). The panel included low-risk HPV, bacteria, viruses, protozoan, yeast, and human cellular DNA. No cross-reactivity or interference in ALINITY m™ HR HPV performance was observed in the presence of the tested microorganisms.

TABLE 16

Microorganisms Tested

Low Risk HPV

HPV 6
HPV 11
HPV 13
HPV 26
HPV 30
HPV 32
HPV 34
HPV 40
HPV 42
HPV 43
HPV 44
HPV 53
HPV 54
HPV 55B
HPV 57
HPV 61
HPV 67
HPV 69
HPV 70
HPV 73
HPV 82
HPV 85

Bacteria

*Bacteroides fragilis*
*Bacteroides ureolyticus*
*Bifidobacterium adolescentis*
*Chlamydia trachomatis*
*Clostridium perfringens*
*Corynebacterium genitalium*
*Entercoccus faecalis*
*Enterobacter cloacae*
*Escherichia coli*
*Fusobacterium necrophorum*
*Gardnerella vaginalis*
*Haemophilus ducreyi*
*Klebsiella pneumoniae* ss
*ozaenae*
*Lactobacillus acidophilus*
*Mycoplasma genitalium*
*Mycoplasma hominis*
*Neisseria gonorrhoeae*
*Neisseria meningitidis* Serogroup A
*Peptostreptococcus anaerobius*
*Proteus mirabilis*
*Pseudomonas aeruginosa*
*Staphylococcus aureus*
*Staphylococcus epidermidis*
*Streptococcus agalactiae*
*Streptococcus pneumoniae*
*Streptococcus pyogenes*
*Trepenoma pallidum*
*Ureaplasma urealyticum*

Virus

Adenovirus
Cytomegalovirus (CMV)
Epstein Barr Virus (EBV)
Hepatitis B virus (HBV)
Herpes simplex virus I TABLE 16-continued

| Microorganisms Tested |
| --- |
| Herpes simplex virus II |
| Human Herpes virus 3 |
| Hepatitis C virus (HCV) |
| Human immunodeficiency virus (HIV-1) |
| Protozoan |
| Trichomonas vaginalis |
| Yeast |
| Candida albicans |
| Other |
| Human Cellular DNA |

Example 11

This example describes the effect of potentially interfering endogenous and exogenous substances on the ALINITY m™ HR HPV assay.

The effect of potentially interfering endogenous and exogenous substances that may be present in cervical specimens on ALINITY m™ HR HPV performance was assessed by testing HPV negative samples and HPV positive samples (SiHa and HeLa cell lines at 3 times the limit of detection) in THINPREP PRESERVCYT™ solution containing a C33A cell line background. Blood was evaluated at a concentration of 10% (v/v), mucus at 5% (v/v), and peripheral blood mononuclear cells (PBMC) at approximately $1 \times 10^6$ cells/mL. The exogenous interference substances were evaluated at 0.5% (w/v) by spiking into the sample. No interference in ALINITY m™ HR HPV performance was observed in the presence of the tested substances (shown in Table 17).

TABLE 17

| Substances Tested | |
| --- | --- |
| Mucus | Up & Up Lubricating Liquid |
| PBMC | KY Jelly |
| Whole Blood | VCF Concentrative Gel |
| Norforms Deodorant Suppositories | Conceptrol Vaginal Contraceptive Gel |
| Clotrimazole Vaginal Cream | Hydrocortisone |
| Terazol-3 Vaginal Cream | Zovirax |
| Monistat 3 | Up & Up Povidone-Iodine |
| Metrogel-Vaginal | Sigma Acetic Acid |
| KY Warming Liquid | |

Example 12

This example describes the determination of the carryover rate for the ALINITY m™ HR HPV assay.

The carryover rate for ALINITY m™ HR HPV was determined by analyzing 265 replicates of HPV negative samples processed from alternating positions with high concentration HPV positive samples at 10,000,000 copies/mL, from more than 10 runs. HPV was not detected in any HPV negative sample, resulting in an overall carryover rate of 0.0% (95% CI: 0.0% to 1.4%).

Example 13

This example demonstrates the agreement of the ALINITY m™ HR HPV assay between specimen types.

Specimens collected in THINPREP PRESERVCYT™ solution and with the ALINITY Cervi-Collect Specimen Collection Kit and from the same 277 patients were tested with ALINITY m™ HR HPV. As shown in Table 18, the overall percent agreement between the ALINITY m™ HPV interpretations of the two specimen types was 94.6% (262/277; 95% CI: 91.3% to 96.7%), with an average positive agreement of 93.4% (214/229; 95% CI: 89.7% to 96.5%) and an average negative agreement of 95.4% (310/325; 95% CI: 92.7% to 97.6%).

TABLE 18

Agreement between Cervi-Collect and PreservCyt Specimens

| | | Cervi-Collect | |
| --- | --- | --- | --- |
| | | HR HPV Detected | Not Detected |
| PreservCyt | HR HPV Detected | 107 | 8 |
| | Not Detected | 7 | 155 |

Specimens collected in SUREPATH™ preservative fluid and THINPREP PRESERVCYT™ solution from the same 276 patients were tested with ALINITY m™ HR HPV. As shown in Table 19, the overall percent agreement between the ALINITY m™ HPV interpretations of the two specimen types was 93.8% (259/276; 95% CI: 90.4% to 96.1%), with an average positive agreement of 91.5% (184/201; 95% CI: 87.2% to 95.1%) and an average negative agreement of 95.2% (334/351; 95% CI: 92.6% to 97.3%).

TABLE 19

Agreement between SUREPATH ™ and PRESERVCYT ™ Specimens

| | | SUREPATH ™ | |
| --- | --- | --- | --- |
| | | HR HPV Detected | Not Detected |
| PreservCyt | HR HPV Detected | 92 | 10 |
| | Not Detected | 7 | 167 |

The aliquots of 119 PRESERVCYT™ specimens that were removed both prior to and after cytological processing (i.e., pre-cytology and post-cytology samples) were tested with THE ALINITY m™ HR HPV assay. As shown in Table 20, the overall percent agreement between the ALINITY m™ HPV interpretations of the pre-cytology and post-cytology samples (Table 14) was 97.5% (116/119; 95% CI: 92.8% to 99.1%), with an average positive agreement of 97.1% (102/105; 95% CI: 93.2% to 100.0%) and an average negative agreement of 97.7% (130/133; 95% CI: 94.7% to 100.0%).

TABLE 20

Agreement between Pre-Cytology and Post-Cytology PRESERVCYT ™ Samples

| | | Post-Cytology | |
| --- | --- | --- | --- |
| | | HR HPV Detected | Not Detected |
| Pre-Cytology | HR HPV Detected | 51 | 3 |
| | Not Detected | 0 | 65 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. The phrase "consisting essentially of" also is construed to be an open-ended phrase meant to include steps or materials which do not materially affect the basic and novel characteristics of a described product or method. The phrase "consisting of" is construed to be a closed phrase which excludes any element, step, or ingredient not explicitly specified in the specification or claims. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A set of oligonucleotide sequences for amplifying and detecting human papilloma virus (HPV) of genotype 16, 18, 31, 33, 35, 39, 45, 51, 52, 56, 58, 59, 66, and/or 68 in a sample, which comprises:
  (a) forward primer oligonucleotide sequences comprising SEQ ID NO: 1, SEQ ID NO: 2, SEQ ID NO: 3, and SEQ ID NO: 4;
  (b) reverse primer oligonucleotide sequences comprising SEQ ID NO: 5 and SEQ ID NO: 6;
  (c) a first probe oligonucleotide sequence comprising SEQ ID NO: 7 or SEQ ID NO: 25 which specifically hybridizes to HPV genotype 16;
  (d) a second probe oligonucleotide sequence comprising SEQ ID NO: 8 which specifically hybridizes to HPV genotype 18;
  (e) a third probe oligonucleotide sequence comprising SEQ ID NO: 9 or SEQ ID NO: 26 which specifically hybridizes to HPV genotype 31;
  (f) a fourth probe oligonucleotide sequence comprising SEQ ID NO: 10 or SEQ ID NO: 27 which specifically hybridizes to HPV genotype 33;
  (g) a fifth probe oligonucleotide sequence comprising SEQ ID NO: 11 which specifically hybridizes to HPV genotype 45;
  (h) a sixth probe oligonucleotide sequence comprising SEQ ID NO: 12 or SEQ ID NO: 28 which specifically hybridizes to HPV genotype 52;
  (i) a seventh probe oligonucleotide sequence comprising SEQ ID NO: 13 or SEQ ID NO: 29 which specifically hybridizes to HPV genotype 58;
  (j) an eighth probe oligonucleotide sequence comprising SEQ ID NO: 14 which specifically hybridizes to HPV genotype 35;
  (k) a ninth probe oligonucleotide sequence comprising SEQ ID NO: 15 or SEQ ID NO: 30 which specifically hybridizes to HPV genotype 39;
  (l) a tenth probe oligonucleotide sequence comprising SEQ ID NO: 16 or SEQ ID NO: 31 which specifically hybridizes to HPV genotype 51;
  (m) an eleventh probe oligonucleotide sequence comprising SEQ ID NO: 17 or SEQ ID NO: 32 which specifically hybridizes to HPV genotype 56;
  (n) a twelfth probe oligonucleotide sequence comprising SEQ ID NO: 18 which specifically hybridizes to HPV genotype 59;
  (o) a thirteenth probe oligonucleotide sequence comprising SEQ ID NO: 19 which specifically hybridizes to HPV genotype 66;
  (p) a fourteenth probe oligonucleotide sequence comprising SEQ ID NO: 20 which specifically hybridizes to HPV genotype 68a;
  (q) a fifteenth probe oligonucleotide sequence comprising SEQ ID NO: 21 which specifically hybridizes to HPV genotype 68b, wherein each of the probe oligonucleotide sequences of (c)-(q) comprises a detectable label.

2. The set of claim 1, wherein (i) each of the first, second, and fifth probe oligonucleotide sequences comprises a different detectable label, (ii) each of the third, fourth, sixth, and seventh probe oligonucleotide sequences comprises the same detectable label, and (iii) each of the eighth through fifteenth probe oligonucleotides comprises the same detectable label, and wherein the detectable labels of (i), (ii), and (iii) are different.

3. The set of claim 1, further comprising:
  (r) an internal control forward primer oligonucleotide sequence comprising SEQ ID NO: 22,
  (s) an internal control reverse primer oligonucleotide sequence comprising SEQ ID NO: 23, and
  (t) an internal control probe oligonucleotide sequence comprising SEQ ID NO: 24 and a detectable label.

4. The set of claim 1, wherein the detectable label is a fluorophore.

5. The set of claim 1, wherein each of the probe oligonucleotide sequences further comprises a quencher moiety.

6. A method for detecting human papilloma virus (HPV) of genotype 16, 18, 31, 33, 35, 39, 45, 51, 52, 56, 58, 59, 66, and/or 68 in a sample suspected of containing HPV, which method comprises:
  (a) contacting a sample obtained from a human with the set of oligonucleotide sequences of claim 1 and reagents for amplification and detection of nucleic acid sequences,
  (b) amplifying one or more target HPV nucleic acid sequences present in the sample,
  (c) hybridizing one or more of the oligonucleotide probes to the one or more amplified target HPV nucleic acid sequences,
  (d) detecting hybridization of the one or more probe oligonucleotide sequences to the one or more amplified target HPV nucleic acid sequences by assessing a signal from each of the detectable labels, whereby (i) the presence of one or more signals indicates hybridization of the one or more probe oligonucleotide sequences to the one or more target HPV nucleic acid sequences and the presence of genotype 16, 18, 31, 33, 35, 39, 45, 51, 52, 56, 58, 59, 66, and/or 68 HPV in the sample, and (ii) the absence of signals indicates the absence of HPV in the sample.

7. The method of claim 6, wherein the sample comprises cervical tissue, blood, serum, plasma, saliva, urine, vaginal fluid, or semen.

8. A kit for detecting human papilloma virus (HPV) of genotype 16, 18, 31, 33, 35, 39, 45, 51, 52, 56, 58, 59, 66, and/or 68 in a sample comprising:

(a) the set of oligonucleotide sequences of claim 1;

(b) reagents for amplifying and detecting nucleic acid sequences; and (c) instructions for use.

9. The kit of claim 8, wherein the oligonucleotide sequences and reagents are lyophilized.

\* \* \* \* \*

SEQUENCE LISTING

```
<160> NUMBER OF SEQ ID NOS: 32

<210> SEQ ID NO 1
<211> LENGTH: 25
<212> TYPE: DNA
<213> ORGANISM: Artificial sequence
<220> FEATURE:
<223> OTHER INFORMATION: Synthetic

<400> SEQUENCE: 1
tatttgttac tgtggtagat actac                                           25

<210> SEQ ID NO 2
<211> LENGTH: 29
<212> TYPE: DNA
<213> ORGANISM: Artificial sequence
<220> FEATURE:
<223> OTHER INFORMATION: Synthetic

<400> SEQUENCE: 2
caattgtttg ttactgttgt ggatactac                                       29

<210> SEQ ID NO 3
<211> LENGTH: 25
<212> TYPE: DNA
<213> ORGANISM: Artificial sequence
<220> FEATURE:
<223> OTHER INFORMATION: Synthetic

<400> SEQUENCE: 3
tttttattac ctgtgttgat actac                                           25

<210> SEQ ID NO 4
<211> LENGTH: 25
<212> TYPE: DNA
<213> ORGANISM: Artificial sequence
<220> FEATURE:
```

```
<223> OTHER INFORMATION: Synthetic

<400> SEQUENCE: 4
tatttgttac tgttgttgat actac                                        25

<210> SEQ ID NO 5
<211> LENGTH: 28
<212> TYPE: DNA
<213> ORGANISM: Artificial sequence
<220> FEATURE:
<223> OTHER INFORMATION: Synthetic

<400> SEQUENCE: 5
gaaaaataaa ctgtaaatca tattcctc                                     28

<210> SEQ ID NO 6
<211> LENGTH: 35
<212> TYPE: DNA
<213> ORGANISM: Artificial sequence
<220> FEATURE:
<223> OTHER INFORMATION: Synthetic

<400> SEQUENCE: 6
tgaaaaataa actgtaaatc atattcttca ccatg                             35

<210> SEQ ID NO 7
<211> LENGTH: 20
<212> TYPE: DNA
<213> ORGANISM: Artificial sequence
<220> FEATURE:
<223> OTHER INFORMATION: Synthetic

<400> SEQUENCE: 7
ctgccatatc tacttcagaa                                              20

<210> SEQ ID NO 8
<211> LENGTH: 22
<212> TYPE: DNA
<213> ORGANISM: Artificial sequence
<220> FEATURE:
<223> OTHER INFORMATION: Synthetic

<400> SEQUENCE: 8
cacagtctcc tgtacctggg ca                                           22

<210> SEQ ID NO 9
<211> LENGTH: 20
<212> TYPE: DNA
<213> ORGANISM: Artificial sequence
<220> FEATURE:
<223> OTHER INFORMATION: Synthetic

<400> SEQUENCE: 9
aagtagtaat tttaaagagt                                              20

<210> SEQ ID NO 10
<211> LENGTH: 19
<212> TYPE: DNA
<213> ORGANISM: Artificial sequence
<220> FEATURE:
<223> OTHER INFORMATION: Synthetic

<400> SEQUENCE: 10
atgcacacaa gtaactagt                                               19
```

<210> SEQ ID NO 11
<211> LENGTH: 22
<212> TYPE: DNA
<213> ORGANISM: Artificial sequence
<220> FEATURE:
<223> OTHER INFORMATION: Synthetic

<400> SEQUENCE: 11
cctactaagt ttaagcagta ta                                            22

<210> SEQ ID NO 12
<211> LENGTH: 14
<212> TYPE: DNA
<213> ORGANISM: Artificial sequence
<220> FEATURE:
<223> OTHER INFORMATION: Synthetic

<400> SEQUENCE: 12
aaaaaggaaa gcac                                                     14

<210> SEQ ID NO 13
<211> LENGTH: 19
<212> TYPE: DNA
<213> ORGANISM: Artificial sequence
<220> FEATURE:
<223> OTHER INFORMATION: Synthetic

<400> SEQUENCE: 13
tgacattatg cactgaagt                                                19

<210> SEQ ID NO 14
<211> LENGTH: 19
<212> TYPE: DNA
<213> ORGANISM: Artificial sequence
<220> FEATURE:
<223> OTHER INFORMATION: Synthetic

<400> SEQUENCE: 14
ctgtgtgttc tgctgtgtc                                                19

<210> SEQ ID NO 15
<211> LENGTH: 14
<212> TYPE: DNA
<213> ORGANISM: Artificial sequence
<220> FEATURE:
<223> OTHER INFORMATION: Synthetic

<400> SEQUENCE: 15
tccatacctt ctac                                                     14

<210> SEQ ID NO 16
<211> LENGTH: 19
<212> TYPE: DNA
<213> ORGANISM: Artificial sequence
<220> FEATURE:
<223> OTHER INFORMATION: Synthetic

<400> SEQUENCE: 16
ttagcactgc cactgctgc                                                19

<210> SEQ ID NO 17
<211> LENGTH: 19
<212> TYPE: DNA
<213> ORGANISM: Artificial sequence
<220> FEATURE:
<223> OTHER INFORMATION: Synthetic

```
<400> SEQUENCE: 17
ttacttaact gttctgtag                                                    19

<210> SEQ ID NO 18
<211> LENGTH: 24
<212> TYPE: DNA
<213> ORGANISM: Artificial sequence
<220> FEATURE:
<223> OTHER INFORMATION: Synthetic

<400> SEQUENCE: 18
attcctaatg tatacacacc tacc                                              24

<210> SEQ ID NO 19
<211> LENGTH: 22
<212> TYPE: DNA
<213> ORGANISM: Artificial sequence
<220> FEATURE:
<223> OTHER INFORMATION: Synthetic

<400> SEQUENCE: 19
caatcaatac cttcgccatg tg                                                22

<210> SEQ ID NO 20
<211> LENGTH: 19
<212> TYPE: DNA
<213> ORGANISM: Artificial sequence
<220> FEATURE:
<223> OTHER INFORMATION: Synthetic

<400> SEQUENCE: 20
ctttgtctac tactactga                                                    19

<210> SEQ ID NO 21
<211> LENGTH: 19
<212> TYPE: DNA
<213> ORGANISM: Artificial sequence
<220> FEATURE:
<223> OTHER INFORMATION: Synthetic

<400> SEQUENCE: 21
cattgtccac tactacaga                                                    19

<210> SEQ ID NO 22
<211> LENGTH: 17
<212> TYPE: DNA
<213> ORGANISM: Artificial sequence
<220> FEATURE:
<223> OTHER INFORMATION: Synthetic

<400> SEQUENCE: 22
gttggtatca aggttac                                                      17

<210> SEQ ID NO 23
<211> LENGTH: 22
<212> TYPE: DNA
<213> ORGANISM: Artificial sequence
<220> FEATURE:
<223> OTHER INFORMATION: Synthetic

<400> SEQUENCE: 23
cctaagggtg ggaaaataga cc                                                22

<210> SEQ ID NO 24
<211> LENGTH: 28
```

```
<212> TYPE: DNA
<213> ORGANISM: Artificial sequence
<220> FEATURE:
<223> OTHER INFORMATION: Synthetic

<400> SEQUENCE: 24
tttctgatag gcactgactc tctctgcc                                        28

<210> SEQ ID NO 25
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: pdC (propyne modified C)
<220> FEATURE:
<221> NAME/KEY: misc_feature
<222> LOCATION: (2)..(2)
<223> OTHER INFORMATION: pdU (propyne modified T)
<220> FEATURE:
<221> NAME/KEY: misc_feature
<222> LOCATION: (4)..(5)
<223> OTHER INFORMATION: pdC (propyne modified C)
<220> FEATURE:
<221> NAME/KEY: misc_feature
<222> LOCATION: (7)..(7)
<223> OTHER INFORMATION: pdU (propyne modified T)
<220> FEATURE:
<221> NAME/KEY: misc_feature
<222> LOCATION: (9)..(9)
<223> OTHER INFORMATION: pdU (propyne modified T)
<220> FEATURE:
<221> NAME/KEY: misc_feature
<222> LOCATION: (10)..(10)
<223> OTHER INFORMATION: pdC (propyne modified C)
<220> FEATURE:
<221> NAME/KEY: misc_feature
<222> LOCATION: (11)..(11)
<223> OTHER INFORMATION: pdU (propyne modified T)
<220> FEATURE:
<221> NAME/KEY: misc_feature
<222> LOCATION: (13)..(13)
<223> OTHER INFORMATION: pdC (propyne modified C)
<220> FEATURE:
<221> NAME/KEY: misc_feature
<222> LOCATION: (14)..(15)
<223> OTHER INFORMATION: pdU (propyne modified T)

<400> SEQUENCE: 25
ctgccatatc tacttcagaa                                                 20

<210> SEQ ID NO 26
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: pdU (propyne modified T)
<220> FEATURE:
<221> NAME/KEY: misc_feature
<222> LOCATION: (7)..(7)
<223> OTHER INFORMATION: pdU (propyne modified T)
<220> FEATURE:
<221> NAME/KEY: misc_feature
<222> LOCATION: (10)..(13)
<223> OTHER INFORMATION: pdU (propyne modified T)
<220> FEATURE:
<221> NAME/KEY: misc_feature
<222> LOCATION: (20)..(20)
```

```
<223> OTHER INFORMATION: pdU (propyne modified T)

<400> SEQUENCE: 26
aagtagtaat tttaaagagt                                              20

<210> SEQ ID NO 27
<211> LENGTH: 19
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: pdU (propyne modified T)
<220> FEATURE:
<221> NAME/KEY: misc_feature
<222> LOCATION: (4)..(4)
<223> OTHER INFORMATION: pdC (propyne modified C)
<220> FEATURE:
<221> NAME/KEY: misc_feature
<222> LOCATION: (6)..(6)
<223> OTHER INFORMATION: pdC (propyne modified C)
<220> FEATURE:
<221> NAME/KEY: misc_feature
<222> LOCATION: (8)..(8)
<223> OTHER INFORMATION: pdC (propyne modified C)
<220> FEATURE:
<221> NAME/KEY: misc_feature
<222> LOCATION: (12)..(12)
<223> OTHER INFORMATION: pdU (propyne modified T)
<220> FEATURE:
<221> NAME/KEY: misc_feature
<222> LOCATION: (15)..(15)
<223> OTHER INFORMATION: pdC (propyne modified C)
<220> FEATURE:
<221> NAME/KEY: misc_feature
<222> LOCATION: (16)..(16)
<223> OTHER INFORMATION: pdU (propyne modified T)
<220> FEATURE:
<221> NAME/KEY: misc_feature
<222> LOCATION: (19)..(19)
<223> OTHER INFORMATION: pdU (propyne modified T)

<400> SEQUENCE: 27
atgcacacaa gtaactagt                                               19

<210> SEQ ID NO 28
<211> LENGTH: 14
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: pdC (propyne modified C)
<220> FEATURE:
<221> NAME/KEY: misc_feature
<222> LOCATION: (14)..(14)
<223> OTHER INFORMATION: pdC (propyne modified C)

<400> SEQUENCE: 28
aaaaaggaaa gcac                                                    14

<210> SEQ ID NO 29
<211> LENGTH: 19
<212> TYPE: DNA
<213> ORGANISM: Artificial sequence
<220> FEATURE:
<223> OTHER INFORMATION: Synthetic
<220> FEATURE:
<221> NAME/KEY: misc_feature
```

```
<222> LOCATION: (1)..(1)
<223> OTHER INFORMATION: pdU (propyne modified T)
<220> FEATURE:
<221> NAME/KEY: misc_feature
<222> LOCATION: (4)..(4)
<223> OTHER INFORMATION: pdC (propyne modified C)
<220> FEATURE:
<221> NAME/KEY: misc_feature
<222> LOCATION: (6)..(7)
<223> OTHER INFORMATION: pdU (propyne modified T)
<220> FEATURE:
<221> NAME/KEY: misc_feature
<222> LOCATION: (9)..(9)
<223> OTHER INFORMATION: pdU (propyne modified T)
<220> FEATURE:
<221> NAME/KEY: misc_feature
<222> LOCATION: (11)..(11)
<223> OTHER INFORMATION: pdC (propyne modified C)
<220> FEATURE:
<221> NAME/KEY: misc_feature
<222> LOCATION: (13)..(13)
<223> OTHER INFORMATION: pdC (propyne modified C)
<220> FEATURE:
<221> NAME/KEY: misc_feature
<222> LOCATION: (14)..(14)
<223> OTHER INFORMATION: pdU (propyne modified T)
<220> FEATURE:
<221> NAME/KEY: misc_feature
<222> LOCATION: (19)..(19)
<223> OTHER INFORMATION: pdU (propyne modified T)

<400> SEQUENCE: 29
tgacattatg cactgaagt                                              19

<210> SEQ ID NO 30
<211> LENGTH: 14
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: pdU (propyne modified T)
<220> FEATURE:
<221> NAME/KEY: misc_feature
<222> LOCATION: (2)..(3)
<223> OTHER INFORMATION: pdC (propyne modified C)
<220> FEATURE:
<221> NAME/KEY: misc_feature
<222> LOCATION: (5)..(5)
<223> OTHER INFORMATION: pdU (propyne modified T)
<220> FEATURE:
<221> NAME/KEY: misc_feature
<222> LOCATION: (7)..(8)
<223> OTHER INFORMATION: pdC (propyne modified C)
<220> FEATURE:
<221> NAME/KEY: misc_feature
<222> LOCATION: (9)..(10)
<223> OTHER INFORMATION: pdU (propyne modified T)
<220> FEATURE:
<221> NAME/KEY: misc_feature
<222> LOCATION: (11)..(11)
<223> OTHER INFORMATION: pdC (propyne modified C)
<220> FEATURE:
<221> NAME/KEY: misc_feature
<222> LOCATION: (12)..(12)
<223> OTHER INFORMATION: pdU (propyne modified T)
<220> FEATURE:
<221> NAME/KEY: misc_feature
<222> LOCATION: (14)..(14)
<223> OTHER INFORMATION: pdC (propyne modified C)

<400> SEQUENCE: 30
tccatacctt ctac                                                   14
```

-continued

```
<210> SEQ ID NO 31
<211> LENGTH: 19
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: pdU (propyne modified T)
<220> FEATURE:
<221> NAME/KEY: misc_feature
<222> LOCATION: (5)..(5)
<223> OTHER INFORMATION: pdC (propyne modified C)
<220> FEATURE:
<221> NAME/KEY: misc_feature
<222> LOCATION: (7)..(7)
<223> OTHER INFORMATION: pdC (propyne modified C)
<220> FEATURE:
<221> NAME/KEY: misc_feature
<222> LOCATION: (8)..(8)
<223> OTHER INFORMATION: pdU (propyne modified T)
<220> FEATURE:
<221> NAME/KEY: misc_feature
<222> LOCATION: (10)..(10)
<223> OTHER INFORMATION: pdC (propyne modified C)
<220> FEATURE:
<221> NAME/KEY: misc_feature
<222> LOCATION: (13)..(13)
<223> OTHER INFORMATION: pdC (propyne modified C)
<220> FEATURE:
<221> NAME/KEY: misc_feature
<222> LOCATION: (14)..(14)
<223> OTHER INFORMATION: pdU (propyne modified T)
<220> FEATURE:
<221> NAME/KEY: misc_feature
<222> LOCATION: (16)..(16)
<223> OTHER INFORMATION: pdC (propyne modified C)
<220> FEATURE:
<221> NAME/KEY: misc_feature
<222> LOCATION: (17)..(17)
<223> OTHER INFORMATION: pdU (propyne modified T)
<220> FEATURE:
<221> NAME/KEY: misc_feature
<222> LOCATION: (19)..(19)
<223> OTHER INFORMATION: pdC (propyne modified C)

<400> SEQUENCE: 31
ttagcactgc cactgctgc                                                19

<210> SEQ ID NO 32
<211> LENGTH: 19
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: pdU (propyne modified T)
<220> FEATURE:
<221> NAME/KEY: misc_feature
<222> LOCATION: (4)..(4)
<223> OTHER INFORMATION: pdC (propyne modified C)
<220> FEATURE:
<221> NAME/KEY: misc_feature
<222> LOCATION: (5)..(6)
<223> OTHER INFORMATION: pdU (propyne modified T
<220> FEATURE:
<221> NAME/KEY: misc_feature
<222> LOCATION: (9)..(9)
<223> OTHER INFORMATION: pdC (propyne modified C)
<220> FEATURE:
<221> NAME/KEY: misc_feature
<222> LOCATION: (10)..(10)
<223> OTHER INFORMATION: pdU (propyne modified T
```

```
<220> FEATURE:
<221> NAME/KEY: misc_feature
<222> LOCATION: (12)..(13)
<223> OTHER INFORMATION: pdU (propyne modified T)
<220> FEATURE:
<221> NAME/KEY: misc_feature
<222> LOCATION: (14)..(14)
<223> OTHER INFORMATION: pdC (propyne modified C)
<220> FEATURE:
<221> NAME/KEY: misc_feature
<222> LOCATION: (15)..(15)
<223> OTHER INFORMATION: pdU (propyne modified T)
<220> FEATURE:
<221> NAME/KEY: misc_feature
<222> LOCATION: (17)..(17)
<223> OTHER INFORMATION: pdU (propyne modified T)

<400> SEQUENCE: 32
ttacttaact gttctgtag                                                19
```